US007326683B2

(12) United States Patent
Molina

(10) Patent No.: US 7,326,683 B2
(45) Date of Patent: Feb. 5, 2008

(54) TREATMENT OF MEMBRANE-ASSOCIATED DISEASES AND DISORDERS USING LANTIBIOTIC CONTAINING COMPOSITIONS

(75) Inventor: Luis Molina, Durham, NC (US)

(73) Assignee: Molichem Medicines, Inc., Chapel Hill, NC (US)

( * ) Notice: Subject to any disclaimer, the term of this patent is extended or adjusted under 35 U.S.C. 154(b) by 29 days.

(21) Appl. No.: 11/124,490

(22) Filed: May 6, 2005

(65) Prior Publication Data

US 2005/0250682 A1    Nov. 10, 2005

Related U.S. Application Data

(60) Provisional application No. 60/569,473, filed on May 6, 2004.

(51) Int. Cl.
*A61K 38/02*    (2006.01)
*A61K 38/12*    (2006.01)

(52) U.S. Cl. .............................................. 514/9; 514/2
(58) Field of Classification Search .................... None
See application file for complete search history.

(56) References Cited

U.S. PATENT DOCUMENTS

| | | | |
|---|---|---|---|
| 4,209,505 A | 6/1980 | Mikhail | |
| 5,071,644 A * | 12/1991 | Viegas et al. ............. | 514/772.7 |
| 5,082,653 A * | 1/1992 | Pan et al. ...................... | 424/54 |
| 5,137,728 A | 8/1992 | Bawa | |
| 5,304,540 A * | 4/1994 | Blackburn et al. ............. | 514/2 |
| 5,512,269 A | 4/1996 | Molina y Vedia et al. | |
| 5,641,781 A | 6/1997 | Cuberes-Altisent et al. | |
| 5,651,957 A | 7/1997 | Molina y Vedia et al. | |
| 5,683,675 A | 11/1997 | Molina y Vedia et al. | |
| 5,716,931 A | 2/1998 | Molina y Vedia et al. | |
| 5,849,706 A | 12/1998 | Molina y Vedia et al. | |
| 5,900,407 A | 5/1999 | Yerxa et al. | |
| 5,968,913 A | 10/1999 | LaCroix et al. | |
| 5,972,988 A | 10/1999 | Macias | |
| 5,981,473 A | 11/1999 | Barefoot et al. | |
| 5,985,823 A * | 11/1999 | Goldstein ...................... | 514/2 |
| 6,027,715 A | 2/2000 | Poznelo | |
| 6,043,219 A | 3/2000 | Iandolo et al. | |
| 6,136,794 A | 10/2000 | Cook et al. | |
| 6,159,952 A | 12/2000 | Shaffer et al. | |
| 6,200,551 B1 | 3/2001 | Morgan | |
| 6,221,357 B1 | 4/2001 | Bok et al. | |
| 6,268,380 B1 | 7/2001 | Tjoeng et al. | |
| 6,277,855 B1 | 8/2001 | Yerxa | |
| 6,291,469 B1 | 9/2001 | Fisher et al. | |
| 6,315,996 B1 | 11/2001 | O'Callaghan | |
| 6,319,908 B1 | 11/2001 | Yerxa et al. | |
| 6,331,529 B1 | 12/2001 | Yerxa et al. | |
| 6,348,589 B1 | 2/2002 | Pendergast et al. | |
| 6,387,886 B1 | 5/2002 | Montgomery et al. | |
| 6,420,347 B1 | 7/2002 | Jacobus et al. | |
| 6,423,694 B1 | 7/2002 | Drutz et al. | |
| 6,423,721 B1 | 7/2002 | Harris et al. | |
| 6,444,695 B1 | 9/2002 | Mahajan et al. | |
| 6,448,276 B1 | 9/2002 | Yerxa | |
| 6,451,288 B1 | 9/2002 | Boucher et al. | |
| 6,462,028 B2 | 10/2002 | Pendergast et al. | |
| 6,489,335 B2 | 12/2002 | Peyman | |
| 6,548,658 B2 | 4/2003 | Yerxa | |
| 6,565,861 B1 | 5/2003 | Tiffany et al. | |
| 6,569,903 B2 | 5/2003 | Honma et al. | |
| 6,596,725 B2 | 7/2003 | Peterson et al. | |
| 6,627,215 B1 * | 9/2003 | Dale et al. ................... | 424/443 |
| 6,656,920 B2 | 12/2003 | Fox et al. | |
| 6,673,779 B2 | 1/2004 | Jacobus et al. | |
| 6,693,109 B2 | 2/2004 | Fisher et al. | |
| 6,713,458 B1 | 3/2004 | Yerxa et al. | |
| 6,716,813 B2 | 4/2004 | Lim et al. | |
| 2003/0157074 A1 * | 8/2003 | Mitrani ..................... | 424/93.21 |
| 2004/0033955 A1 | 2/2004 | Catania et al. | |
| 2004/0192581 A1 * | 9/2004 | Walsh et al. ................... | 514/2 |
| 2005/0250681 A1 * | 11/2005 | Molina .......................... | 514/9 |

FOREIGN PATENT DOCUMENTS

| | | |
|---|---|---|
| JP | 2002-053492 A2 | 2/2002 |
| WO | WO 94/05251 A1 * | 3/1994 |
| WO | WO 94/28726 A2 | 12/1994 |
| WO | WO 98/34593 A1 | 8/1998 |
| WO | WO 99/09998 A1 | 3/1999 |
| WO | WO 01/80844 A2 | 11/2001 |
| WO | WO 01/87288 A2 | 11/2001 |
| WO | WO 01/87913 A2 | 11/2001 |
| WO | WO 02/09702 A2 | 2/2002 |
| WO | WO 02/16381 A2 | 2/2002 |
| WO | WO 2004/037167 A2 | 5/2004 |

OTHER PUBLICATIONS

Afzelius, B.A., "A human syndrome caused by immotile cilia," *Science*,193(4250):317-319(Jul. 23, 1976).
Afzelius, B.A., "Lack of dynein arms in immotile human spermatozoa," *J. Cell. Biol.*, 66(2):225-232 (Aug. 1975).
Ballenger, J.J., "Acquired ultrastructural alterations of respiratory cilia and clinical disease. A review," *Ann. Otol. Rhinol. Laryngol.*, 97(3 Pt. 1):253-258 (May-Jun. 1988).
Baudouin, C., "The Pathology of Dry Eye," *Surv. Ophthalmol.* 45 Suppl. 2: S211-S220 (Mar. 2001).
Boschelli, D.H., et al., "Inhibition of E-selectin-, ICAM-1-, and VCAM-1-mediated cell adhesion by benzo[b]thiophene-, benzofuran-, indole-, and naphthalene-2-carboxamides: identification of PD 144795 as an antiinflammatory agent," *J. Med. Chem.*, 38(22):4597-4614 (Oct. 27, 1995).

(Continued)

*Primary Examiner*—Jeffrey Edwin Russel
(74) *Attorney, Agent, or Firm*—King & Spalding

(57) ABSTRACT

Compositions useful for treating membrane-associated diseases, conditions, and disorders, including inflammatory diseases, dry mouth, primary ciliary dyskinesia and platelet aggregating disorders, are disclosed which comprise at least one lantibiotic compound. Also disclosed are pharmaceutical compositions and methods of treatment for membrane-associated diseases such as inflammation and dermal irritation, as well as use of such compositions in the treatment of membrane-associated diseases, wherein the pharmaceutical compositions contain at least one lantibiotic.

19 Claims, No Drawings

OTHER PUBLICATIONS

Boucher, R., et al., "Mechanisms and therapeutic actions of uridine triphosphates in the lungs," *Adenosine and Adenine Nucleotides: From Molecular Biology to Integrative Physiology*, (L. Belardelli, et al., Eds., Alumwer Academic Publishers, Boston, 1995), pp. 525-532.

Bowie, E.M., et al., "Corticosteroids, central serous chorioretinopathy, and neurocysticercosis," *Arch. Ophthalmol.*, 122(2):281-283 (Feb. 2004).

Brewitt, H., et al., "Dry Eye Disease: The Scale of the Problem," *Surv. Ophthalmol.* 45 Suppl. 2: S199-S202 Mar. 2001).

Brown, C.G., et al., "Clinical consequences of oral mucositis," *Semin. Oncol. Nurs.*, 20(1):16-21 (Feb. 2004).

Chang, Y.H., et al., Eur. J. Pharmacol., 69(2):155-164 (Jan. 16, 1981). Effects of pharmacologic agents on the reversed passive Arthus reaction in the rat.

Cloutier, M.M., et al., "Duramycin enhances chloride channel activity in cystic fibrosis nasal epithelial cells." *Pediatric Pulmonology*, 2(Supplement):99 (Abstract 15) (1988).

Cloutier, M.M., et al., "Duramycin enhances chloride secretion in airway epithelium," *Am J Physiol.* —Cell Physiol., Sep.;259(3 Pt 1):C450-C454 (Sep. 1990).

De Nijs, E., et al., "The adverse effects of corticosteroids in central serous chorioretinopathy" *Bull. Soc. Belge Ophtalmol.*, 289:35-41 (2003).

Diamond, M.S., et al., "The dynamic regulation of integrin adhesiveness" *Current Biology*, 4(6):506-517 (Jun. 1, 1994).

Forrest, J.B., et al., "Activation of nasal cilia in immotile cilia syndrome," *Am. Rev. Respir. Dis.*, 120(3):511-515 (Sep. 1979).

Foulks, G.N., "The evolving treatment of dry eye," *Ophthalmol. Clin. North Am.*, 16(1):29-35 (Mar. 2003).

Friedlander, A.H., et al., "Late-life depression: psychopathology, medical interventions, and dental implications," *Oral Surg. Oral Med. Oral Pathol. Oral Radiol. Endod.*, 94(4):404-412 (Oct. 2002).

Greenstone, M.A., "Hydrocephalus and primary ciliary dyskinesia," *Arch. Dis. Child.*, 59(5), 481-482 (May 1984).

Gross, E., et al.,"Subtilin, VI: Die Struktur des Subtilins," *Z. Physiol. Chem.*,354:810-812 (Jul. 1973).

Hayashi, F., et al., "The structure of PA48009: The revised structure of duramycin," *J. Antibiotics* (Tokyo), LXIII(11):1421-1430 (Nov. 1990).

Hechard, Y., et al., "Mode of action of modified and unmodified bacteriocins from Gram-positive bacteria," *Biochimie*, 84(5-6):545-557 (May-Jun. 2002).

Hendrickson, R.G., et al., "Pilocarpine toxicity and the treatment of xerostomia," *J. Emerg. Med.*, 26(4):429-432 (May 2004).

Kellerman, D.J., "y2Y$_2$ Receptor agonists: a new class of medication targeted at improved mucociliary clearance," *Chest*, 121(5 Suppl.):201S-205S (May 2002).

Kellner, R., et al., "Gallidermin: a new lanthionine-containing polypeptide antibiotic," *Eur. J. Biochem.* 177(1), 53-59 (Oct. 15, 1988).

Kessler, H., et al., "204. The structure of the polycyclic nonadecapeptide Ro 09-0198," *Helv. Chim. Acta*, 71:1924-1929 (1988).

Kettenring, J.K., et al., "Sequence determination of actagardine, a novel lantibiotic, by hormonuclear 2D NMR spectroscopy," *J. Antibiotics*, XLIII(9):1082-1088 (Sep. 1990).

Kishimoto, T.K., et al., "Integrins, ICAMs, and selectins: role and regulation of adhesion molecules in neutrophil recruitment to inflammatory sites," *Adv. Pharmacol.*, 25:117-169 (1994).

Knowles, M.R., et al., "Activation by extracellular nucleotides of chloride secretion in the airway epithelia of patients with cystic fibrosis," *N. Eng. J. Med.*, 325(8):533-538 (Aug. 22, 1991).

Lansley, A.B., et al., "Control of the beat cycle of respiratory tract cilia by Ca2+and cAMP.," *Am. J. Physiol.*, 263(2 Pt. 1):L232-L242 (Aug. 1992).

Lethem, M.L., et al., "Nucleotide regulation of goblet cells in human airway epithelial explants: normal exocytosis in cystic fibrosis ," *Am. J. Respir. Cell. Mol. Biol.*, 9(3):315-322 (Sep. 1993).

Locker, D., "Dental status, xerostomia and the oral health-related quality of life of an elderly institutionalized population," *Spec. Care Dentist*, 23(3):86-93 (2003).

McNulty, M.J., et al., "Pharmacokinetics and tissue distribution of the nonadecapeptide Moli1901 in rats and mice," *Xenobiotica*, Feb.;33(2):197-210 (Feb. 2003).

Monnet, D., et al., "Ophthalmic findings and frequency of extraocular manifestations in patients with HLA-B27 uveitis: a study of 175 cases," *Ophthalmology*, 111(4):802-809 (Apr. 2004).

Musza, L.L., et al., "Potent new cell adhesion inhibitors from the root of *trichilia rubra*," *Tetrahedron*, 50(39):11369-11378 (1994).

Nakamura, S., et al., "Inhibitory effect of duramycin on partial reactions catalyzed by (Na+,K+)-adenosinetriphosphatase from dog kidney," *Biochem.*, 23(2):385-389 (Jan. 17, 1984).

Nussenblatt, R.B., et al., "Cyclosporine: immunology, pharmacology and therapeutic uses," *Survey of Ophthalmology*, 31(3):159-169 (Nov.-Dec. 1986).

O'Neil, M.J., Sr. Ed., et al., The Merck Index: An Encyclopedia of Chemicals, Drugs, and Biologicals, 13$^{th}$ Ed., O'Neil, M.J. Sr. Ed. (Merck & Co., Inc., Whitehouse Station, New Jersey, 2001), entry No. 2781 ("Cyclosporin A"), p. 480.

Pedersen, M., "Ciliary activity and pollution," *Lung*, 168 Suppl.: 368-376 (1990).

Pridham, T.G., et al., "Antibiotics against plant disease. II. Effective agents produced by streptomyces cinnamomeus forma azacoluta F. Nov.," *Phytopathology*, 46:575-581 (Oct. 1956).

Roberts, M., et al., "Stimulation of sodium transport by duramycin in cultured human colonic epithelia," *J. Pharmacol. Exp. Ther.*, 259(3):1050-1058 (Dec. 1991).

Sahl, H.-G., "Influence of the Staphyloccinlike peptide Pep 5 on membrane potential of bacterial cells and cytoplasmic membrane vesicles," *J. Bacteriol.*, 162(2):833-836 (May 1985).

Sanfilippo, P.J., et al., "Novel thiazole based heterocycles as inhibitors of LFA-1/ICAM-1 mediated cell adhesion," *J. Med. Chem.*, 38(7):1057-1059 (Mar. 31, 1995).

Schalenbourg, A., et al., "Corticosteroid-induced central serous chorioretinopathy in patients with ocular inflammatory disorders," *Klinische Monatsblätter Für Augenheilkunde*, 219(4):264-267 (Apr. 2002).

Schidlow, D.V., "Primary ciliary dyskinesia (the immotile cilia syndrome)," *Ann. Allergy*, 73(6):457-468 (Dec. 1994).

Schnell, N., et al., "Prepeptide sequence of epidermin, a ribosomally synthesized antibiotic with four sulphide-rings," *Nature*, 333(6170):276-278 (May 19, 1988).

Shotwell, O.L., et al., "Antibiotics against plant disease. III. Duramycin, a new antibiotic from IStreptomyces cinnaomoeus forma *azacoluta*," *J. Am. Chem. Soc.* 80:3912-3915 (Aug. 5, 1958).

Sleigh, M.A., "Primary ciliary dyskinesia," *Lancet*, 2(8244):476 (Aug. 29, 1981).

Springer,T.A., "Adhesion receptors of the immune system.," *Nature*, 346(6283):425-434 (Aug. 2, 1990).

Stack, K.M., et al., "Comparison of plaque and gingival status of three groups of saliva hypofunction patients," (76th General session of the International Association for Dental Research. Nice, France, Jun. 24-27, 1998) J. Dental Research, 77(Special Issue No. B):979 (1998) .Abstract No. 2779.

Valerius, N.H., "Defective neutrophil motility in patients with primary ciliary dyskinesia," *Eur. J. Clin. Invest.*, 13(6):489-494 (Dec. 1983).

Wakamiya, T., et al., "The structure of ancovenin, a new peptide inhibitor of Angiotensin I Converting Enzyme," *Tetrahedron Lett.,*, 26(5):665-668 (1985).

Wandel, T., et al., "Glaucoma treatment with once-daily levobunolol," *Amer. J. Ophthalmol.*, 101(3):298-304 (Mar. 15, 1986).

\* cited by examiner

TREATMENT OF MEMBRANE-ASSOCIATED DISEASES AND DISORDERS USING LANTIBIOTIC CONTAINING COMPOSITIONS

The application claims priority to U.S. Provisional Application No. 60/569,473, filed May 6, 2004 which is herein incorporated by reference in its entirety.

FIELD OF THE INVENTION

The invention provides compounds and pharmaceutical compositions for the treatment of membrane-associated diseases and, more specifically, provides pharmaceutical compositions containing lantibiotics for use in the treatment of membrane-associated diseases. In particular, pharmaceutical compositions containing duramycin, and methods for their use in the treatment of membrane-associated diseases are disclosed.

BACKGROUND

Membrane-associated diseases, those diseases and disorders whose pathology is directly linked a specific membrane or subset of membranes, have increased in incidence over time. Numerous and varied diseases falling into this category exist (see, "The Merck Manual of Diagnosis and Therapy, 17$^{th}$ Ed.", Berkow, R., et al., Eds., John Wiley & Sons, 1999), but can generally be broken into broader categories, such as inflammatory diseases, ciliary dyskinesias, and platelet aggregation disorders. Concomitant with the numerous types of diseases and disorders falling into this category, numerous approaches to the therapeutic treatment or prevention of these disorders have appeared.

Inflammatory diseases, encompassing arthritis, represent one of the largest categories of membrane-associated diseases. Research spanning the last decade has helped to elucidate the molecular events associated with membrane-associated diseases in the body, especially those events involved in the movement and activation of cells in the immune system. See, generally, Springer, T. *Nature*, 346: pp. 425-434 (1990). Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally, Kishimoto, T. K.; Rothlein; R. R. *Adv. Pharmacol.* 25: 117-138 (1994) and Diamond, M.; Springer, T., *Current Biology*, 4: 506-532 (1994). As a result, a wide variety of anti-inflammatory based compounds have been contemplated as therapeutic agents.

Several small molecules have been described in the literature which are potentially useful in the treatment of membrane-associated disorders related to inflammation. A natural product isolated from the root of *Trichilia rubra* was found to be inhibitory in an in vitro cell binding assay (Musza, L. L.; et al., *Tetrahedron*, 1994, 50, 11369-11378). One series of molecules (Boschelli, D. H.; et al., *J. Med. Chem*, 1994, 37, 717 and Boschelli, D. H.; et al., *J. Med. Chem.* 1995, 38, 4597-4614) was found to be orally active in a reverse passive Arthus reaction, an induced model of inflammation that is characterized by neutrophil accumulation (Chang, Y. H.; et al, *Eur. J Pharmacol.* 1992, 69, 155-164). Another series of molecules was also found to be orally active in a delayed type hypersensitivity reaction in rats (Sanfilippo, P. J.; et al., *J. Med. Chem.* 1995, 38, 1057-1059).

Numerous other classes of compounds have been described in the patent literature as having the potential to alleviate membrane-associated diseases and disorders, including aerosolized antibiotics (U.S. Pat. No. 6,387,886); uridine triphosphate and related compounds (U.S. Pat. No. 6,159,952); 1H-indole-3-glyoxylamide (U.S. Pat. No. 5,972, 988); and a method for the treatment of otitis media and paranasal sinusitis using human defensins, lysozyme and/or lactoferrin as a new class of non-antibiotic antimicrobials (U.S. Pat. No. 6,716,813). U.S. Pat. No. 6,423,721 describes antibiotic-excluded compositions and methods to treat non-infective sinusitis and/or otitis media. The compositions contain a therapeutically effective amount of an anticholinergic antihistamine or a pharmaceutically acceptable salt or solvate thereof; and a pharmaceutically acceptable carrier, as well as methods of administering the same. Additionally, benzimidazoles have been suggested for use in the treatment of conjunctivitis, especially allergic conjunctivitis (U.S. Pat. No. 5,641,781).

Another membrane-associated disease whose incidence has recently increased is oral-membrane disease/disorder xerostomia. Xerostomia occurs when inadequate amounts of saliva are secreted into the mouth, preventing adequate lubrication of the oral cavity and resulting in an uncomfortable oral sensation and difficulty with speaking and swallowing, and in some instances severe cracking of the tongue.

Xerostomia can result from either decreased production of saliva within the glands and/or diminished secretion of saliva from the glands following autonomic stimulation. It is most commonly caused as an unwanted side effect of many classes of prescription medications including anticholinergics, antispasmodics, antihypertensives, antidepressants, anticonvulsants, pain killers, anti-rejection drugs, and antipsychotics, as well as over-the-counter decongestants and antihistamines (Brown, C. G., et al., *Semin Oncol Nurs.*, 20: pp. 16-21 (2004)). These classes of drugs either directly inhibit saliva production within the glands or inhibit its secretion into the mouth by inhibiting the autonomic nervous system (Friedlander, A. H., et al., *Oral Surg Oral Med Oral Pathol Oral Radiol Endod.*, 94: pp. 404-416 (2002)). *Xerostomia* can also occur during states of elevated stress, anxiety, depression, with certain endocrine diseases such as hypothyroidism, during chemotherapy, and with auto-immune disorders such as Sjögren's syndrome. Furthermore, the glands can be destroyed by radiation therapy to the neck, traumatic injury to the neck, neck surgery, or by other direct injury of the gland and its controlling autonomic nerves. The incidence of xerostomia also increases in the elderly (Locker, D., *Spec Care Dentist.*, 23: pp. 86-93 (2003)).

Adequate salivary gland function is critical for protection of the oral cavity and support of oral functions, including speech and oral comfort. In humans saliva is provided by the three paired major salivary glands, (parotid, submandibular and sublingual), and thousands of minor salivary glands which are situated throughout the oral cavity and named based on location (buccal, palatal, labial, etc.). Between meals salivary flow is maintained at a low level of output by endogenous physiologic mechanisms. The unstimulated, or resting, saliva is essential for general oral comfort and is high in antimicrobial and mucoprotective factors. The salivary glands are activated by masticatory and gustatory stimuli during meals, resulting in a marked increase in salivary output. This stimulated output provides support for swallowing, chewing and buffering of microbial acids, but the output quickly falls to the resting level once active stimulation ceases.

In the absence of saliva, oral bacterial effects accelerate. Users of medications that cause xerostomia have been reported to have 10 times the normal level of oral bacteria, and three to four times the normal level of dental decay (study presented at the International Association of Dental Research, Nice, France, 1998). Patients with dry mouth are also more prone to fungal infections, gum disease and (due to xerostomic discomfort in eating some types of foods) malnutrition.

Typical treatments for xerostomia have involved supportive and replacement therapies to restore oral moisture, as well as pharmacologic agents to stimulate the body's own saliva production. Examples of such treatments have included the use of carbamide peroxide (U.S. Pat. No. 6,200,551), pilocarpine (Hendrickson, et. al., *J Emerg Med.*, 26: pp. 429-432 (2004); U.S. Pat. No. 4,209,505), a combination of algae and pectin in a lozenge (U.S. Pat. No. 6,027,715), regular parenteral treatment with interferon-α (Ferraccioli et al.), and the administration of lozenges containing maltose or trehalose (U.S. Pat. No. 6,656,920). Several secretogogues with transient benefits have failed to demonstrate sustained benefit in controlled clinical trials; these include bromhexine, anetholetrithione, pilocarpine, and cevimeline. Side effects have included excessive sweating during treatment with pilocarpine or cevimeline.

A further category of membrane-associated disorders is primary ciliary dyskinesias. Primary ciliary dyskinesia (PCD) is a congenital disease characterized by ultrastructural defects and motility disturbances of cilia, resulting in either absent or abnormal ciliary movement. The most common clinical manifestations of PCD are chronic respiratory disease (e.g., sinusitis, rhinitis, and bronchiectasis) and otitis media. Because PCD patients have either no or severely impaired mucociliary clearance (MCC), the only available mechanism to clear or move secretions is cough. PCD has also been reported to impair the propulsion of spermatozoa, resulting in male infertility. (D. Schidlow, *Ann Alergy*, 73(b): pp. 457-68 (1995)). Typical methods of treating this membrane-associated disorder include administering uridine triphosphates, adenosine triphosphates, cytidine triphosphates, or dinucleoside tetraphosphates and their derivatives thereof to a patient so as to treat this dysfunction of the mucociliary clearance system (see, for example, U.S. Pat. No. 6,673,779). Uridines, especially di(uridine 5')-tetraphosphate (U.S. Pat. Nos. 6,548,658 and 6,713,458) and analogs of both this compound and uridine triphosphate (U.S. Pat. No. 5,968,913; U.S. Pat. No. 6,451,288) have also been suggested for use in controlling membrane-associated diseases such as primary ciliary dyskinesia.

Mucociliary clearance is an important defense mechanism of the human airway and middle/inner ear tract. Coordinated beats of cilia in the nose, trachea, bronchi, and middle ear propel the mucous layer toward the pharynx, carrying along with it microorganisms and other particles captured in the mucus. Normal function of this system depends on the frequency and coordination of ciliary beating and the properties of mucus. There are three components of the mucociliary clearance system: (1) the mucin layer, which is formed by secretion of mucins by goblet cells, (2) cilia, which transport the overlying mucin layer by synchronous beating, and (3) the periciliary liquid layer, which surrounds the cilia and is less viscous than the mucin layer, allowing free movement of the cilia. The electrolyte and water concentration of the periciliary layer is regulated by the luminal epithelial cells. (R. Boucher, et al., Adenosine and Adenine Nudeotides: From Molecular Biology to Integrative Physiology, p. 525-32 entitled "Mechanisms and Therapeutic Actions of Uridine. Triphosphates in the Lung" (L. Belardinelli, et al. ed., Alumwer Academic Publishers, Boston 1995)).

PCD also results in the impairment of cell motility of certain immune system cells, including neutrophils and macrophages. (N. Valerius, Eur J Clin Invest 13, 489-94 (1983)). PCD can be responsible for a form of hydrocephalus caused by ciliary malfunction. (M. Greenstone, Arch Dis Child 59,481-82 (1984)). The incidence of PCD has been calculated to be one in 16,000 live births, and an estimated 50% of affected individuals also have situs inversus (dextrocardia). The triad of bronchiectasis, sinusitis, and situs inversus (dextrocardia) is referred to as Kartageneis syndrome. (M. Sleigh, Lancet ii, 476 (1981)). It has been hypothesized that Kartagener's syndrome is caused by a lack of embryonic ciliary movement, resulting in the random rotation of the archenteron such that in half the cases there is situs inversus (dextrocardia) and in the other half there is normal cardia situs. (B. Afzelius, Science 193, 317-19 (1976)). The clinical course of PCD is characterized primarily by sinus and ear infections early in life with a progressive change to lung/lower airways diseases in adulthood. Chronic airways infections can lead to chronic obstructive changes in the pulmonary tissue, progressive loss of pulmonary function, and eventually death.

A second and more common form of ciliary dyskinesia is the acquired form of the disease. Chronic inflammation caused by severe viral or bacterial respiratory infections, chronic smoking, severe air pollution, chemical or thermal bums to the airways, intubation and mechanical ventilation, and near-drowning can result in changes in ciliary structure including disruption of the cellular membrane, loss or incorporation of microtubules, and formation of compound cilia, all of which can result in abnormal or absent ciliary function. (J. Ballenger Ann Otol Rhinol Laryngol 97 (3 Pt. 1), 253-58 (1988); U Pedersen Lung 168 Suppl., 368-76 (1990)). Respiratory infections which often lead to secondary ciliary dyskinesia include influenza, adult respiratory distress syndrome, and ventilator-associated pneumonia (VAP) in intensive care unit (ICU) patients. In some cases acquired ciliary dyskinesia can be reversed with appropriate and timely intervention; however, permanent damage and/or sustained exposure to the above factors can render the ciliary damage irreversible. The clinical manifestations and course would likely appear similar to PCD with respect to chronic lung infections, progressive loss of pulmonary function, and obstructive pulmonary disease.

The typical mammalian respiratory epithelial ceil contains about 200 cilia. Each cilium has nine peripheral microtubular doublets and two central tubules. Each peripheral doublet contains an A subunit and a B subunit, and each A subunit has a set of curved arms attached to it called the inner and outer dynein arms. These dynein arms contain ATPase-an enzyme which breaks down adenosine triphosphate (ATP), providing the energy for ciliary movement. Because the most common ultrastructural abnormality associated with primary ciliary dyskinesia is the total absence of dynein arms (B. Afzelius, et al, J Cell Biol 66, 225-32 (1975)), researchers began investigating whether extracellular application of ATP and ATPase could activate immotile cilia in vitro. (J. Forrest, et al., Am Rev Resp Dis 120, 511-15 (1979)). Although the results appeared positive, the findings have not been consistently reproduced by others. It was later discovered that extracellular application of $Ca^{2+}$ and cAMP could increase the beat frequency of respiratory tract cilia. (A. Lansley, et al., Am J. Physiol 263, L232-42) (1992)). It has not been definitively established that any therapy can stimulate cilia beat in cases where complete ciliary immotility has been demonstrated. In such cases, it can be of therapeutic benefit to increase hydration of the viscous mucous secretions.

It is known that ATP/UTP stimulates ciliary beat frequency in nasal epithelial cells (R. Boucher, et al., supra); UTP stimulates mucin secretion by goblet cells (M. Lethem, et al., Am J Respir Cel Mol Biol 9, 315-22 (1993)); and UTP stimulates C1 secretion in airway epithelial cells, which increases hydration of the periciliary liquid layer (M. Knowles, et al., N Eng J. Med 325, 533-38 (1991)).

There is an ongoing need in the art for improved therapeutic means to promote clearance of secretions from the sinuses, upper airways, ears, urinary tract, spermatozoa, ovaries, fallopian tubes, neutrophils, and macrophages of a patient.

Another area of interest in the area of membrane-associated diseases and disorders are platelet aggregation disorders, such as fibrinogen-dependent platelet aggregation, thrombin-induced platelet aggregation, and collagen-induced platelet aggregation. The basic mechanism of platelet aggregation has been well-studied. The mechanism starts with a blood vessel injury such as narrowing of the lumen, plaque formation, and the presence of foreign bodies/medical instruments. This injury leads to platelet activation and binding of fibrinogen and ligands. Upon ligand binding, the JAK (Janus-family Kinase) kinases, a family of cytoplasmic protein tyrosine kinases which mediate cytokine receptor signaling, undergo tyrosine phosphorylation and activate the cytoplasmic latent forms of the STAT family transcription factors (Signal Transducers and Activators of Transcription). This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin, the GPIIb/IIIa binding site becomes available to fibrinogen, eventually resulting in platelet aggregation and clot formation. Diseases involving platelet aggregating disorders include the following.

Atherosclerotic cardiovascular disease (ASCVD) is the leading cause of death in most industrial countries. This disease involves large, medium and small arteries throughout the body. In addition to family history, the atherogenic risk factors are known to include smoking, hypertension, diabetes mellitus, cholesterol abnormalities and homocysteinuria. The presence of each additional risk factor markedly aggravates the potential for development of the disease. Although seemingly diverse, the risk factors all damage the artery wall and effect formation of thrombosis.

In the aorta, the largest artery, the artery wall damage can lead to aortic aneurysm or embolism. ASCVD in medium and small arteries can result in sudden occlusion of the vessel or progressive narrowing of the arterial lumen. The symptoms of persons with this disease are dictated by the organs supplied by the effected arteries. Lumenal narrowing of the arteries supplying the heart with blood is called coronary artery disease (CAD). The symptoms include angina, unstable angina, myocardial infarction (MI) and sudden death. Cerebral vascular disease (CVD) symptoms include progressive neural deterioration, transient ischemic attack (TIA), seizures, and cerebral vascular accident (CVA), i.e., stroke. Kidney effects include hypertension, renal infarction and renal failure. Abdominal vascular insufficiency results in abdominal angina and bowel infarction. Peripheral vascular disease (PVD) symptoms include intermittent claudication, gangrene and amputation.

Because atherosclerosis greatly increases the risk of peripheral vascular disease, angina, stroke, some causes of neural degeneration, and heart attacks—the number one cause of death in the USA, a comprehensive approach is needed to address this problem. Despite the broad use of lipid lowering agents, individuals with elevated homocysteine levels are about four times more likely to die of cardiovascular disease than those with normal levels.

Currently accepted clinical treatment of ASCVD includes prescription medications such as beta blockers, angiotensin converting enzyme (ACE) inhibitors, calcium channel blockers, and cholesterol lowering medication. In addition, aspirin is prescribed by cardiologists in many ASCVD conditions. For example, in atherosclerotic heart disease (ASHD), there is evidence of protection from a second MI, if aspirin is used after the sentinel event. Risk of MI is decreased by approximately 50 percent. Vitamins are also currently prescribed by many cardiologists and endocrinologists with intent of preventing both primary (first event), and secondary events.

Many therapeutic approaches have attempted to control platelet aggregation and the resulting membrane-associated diseases by blocking various formation sites, and/or the glycoprotein complex itself. U.S. Pat. No. 6,136,794 describes the use of low molecular weight heparin in combination with a GPIIb/IIa antagonist in order to inhibit platelet aggregation; U.S. Pat. Nos. 6,291,469 and 6,693,109 describe the use of a variety of spiro compounds as inhibitors of fibrinogen-dependent platelet aggregation; creatine kinase inhibitors have also been suggested for use as inhibitors of platelet aggregation (U.S. Pat. No. 6,444,695), as have urea derivatives (U.S. Pat. No. 6,268,380) and flavonoids (U.S. Pat. No. 6,221,357).

Several other compositions, including uridine triphosphate and tetraphosphate, as well as salts thereof (U.S. Pat. No. 6,319,908; EP 1253916A1) and dinucleotide polyphosphate compositions have been described for use in treating vaginal dryness and promoting vaginal secretions (U.S. Pat. No. 6,448,276; U.S. Pat. No. 6,462,028), inhibiting platelet aggregation, treatment of lung diseases (WO 9909998A1), treating ciliary dyskinesia (U.S. Pat. No. 6,420,347), inhibiting platelet aggregation (WO 0216381A3), modulating mucociliary clearance and ciliary beat frequency (U.S. Pat. No. 6,348,589), promoting mucosal hydration (U.S. Pat. No. 6,331,529), and treating bronchitis (U.S. Pat. No. 6,159,952).

All of these molecules, while largely specific to particular membrane-associated diseases, appear to act nonspecifically, or suffer from delivery problems due to poor absorption properties of the compounds. Thus they have shortcomings in potency, selectivity, solubility, and specificity of mechanism, and are unlikely to be satisfactory for therapeutic use.

Thus, based upon the limited success of other chemotherapeutic approaches to membrane-associated diseases to date, there is a need for pharmaceuticals that are suitable for use in the treatment of a variety of membrane-associated diseases and disorders.

It is an object of the present invention to provide improved methods for the treatment of a variety of membrane-associated diseases and disorders.

It is another object of the present invention to provide compositions and formulations for the treatment of membrane-associated diseases and disorders.

SUMMARY OF THE INVENTION

The present invention provides pharmaceutical compositions containing lantibiotics for the treatment of membrane-associated diseases and disorders. Duramycin can increase the hydration of membranes and therefore can be beneficial for the treatment of such disorders. The present invention also provides methods for the treatment of membrane associated diseases and disorders by providing an effective amount of a composition containing at least one lantibiotic, such as duramycin, in a pharmaceutically acceptable formulation to a diseased membrane.

In one embodiment of the present invention, pharmaceutical compositions and formulations containing at least one lantibiotic as described herein for the treatment of membrane-associated disorders and/or diseases are provided, such as inflammation conditions, platelet aggregation, and primary ciliary dyskinesia. In particular, pharmaceutical compositions and formulations containing duramycin for the treatment of such disorders and/or diseases are provided. In another embodiment, the compositions and formulations provided herein can be used to relieve the discomfort or irritation associated with membrane diseases and disorders.

In aspect of the present invention, the compositions and formulation disclosed herein can be used to treat inflammation of any organ, such as, but not limited to the kidney, liver, stomach, bladder, bowels, pancreas, thyroid, heart, and skin. In another embodiment of the present invention, a composition containing at least one lantibiotic is used to treat an inflammatory condition of the central nervous system. In another embodiment, the compositions disclosed herein can be used to treat an inflammatory condition of the immune system, such as, but not limited to autoimmune disease, and/or joint, such as arthritis. In a further embodiment, the compositions and formulations described herein can be used for the treatment of inflammation of the mouth, ears, nose, throat, pharynx, larynx, trachea, sinuses, or upper respiratory tract inflammation. In a particular embodiment, the compositions described herein are not used to treat a disease or disorder of the lung. In another particular embodiment, the compositions described herein are not used to treat a disease or disorder of the eye.

In another aspect of the present invention, a composition containing at least one lantibiotic can be used in a medicament to treat xerostomia. In another embodiment of the present invention, a composition containing at least one lantibiotic is used in a medicament to treat drug-induced xerostomia. In one embodiment, the drug induced xerostomia can be caused by another class of medications, including but not limited to anticholinergics, antispasmodics, antihypertensives, antidepressants, anticonvulsants, pain killers, anti-rejection drugs, anti-pyschotics, decongestants, and/or antihistamines. In a further embodiment, the compositions and formulations described herein can be used to treat xerostomia associated with abnormal physiological states, for example, including, but not limited to elevated stress, anxiety, depression, endocrine disease, autoimmune disorder and/or any other sickness, disorder or disease.

In a further aspect of the present invention, a composition containing at least one lantibiotic can be used in a medicament to treat ciliary dyskinesia. In one embodiment, the ciliary dyskinesia can be a primary ciliary dyskinesia. In another embodiment, the ciliary dyskinesia can be a secondary ciliary dyskinesia. In particular embodiments, the ciliary dyskinesia can affect the mouth, ears, nose, throat, sinuses, upper airways, genito-urinary tract, spermatozoa, ovaries, fallopian tubes and/or any other ciliated region of the body.

In a still further aspect of the present invention, a composition containing at least one lantibiotic can be used to treat or prevent a platelet aggregating disease. In one embodiment, the platelet aggregating disease can be, but is not limited to,: atherosclerotic cardiovascular disease, coronary artery disease, cerebral vascular disease, kidney disease, abdominal vascular insufficiency, and/or peripheral vascular disease. In an additional embodiment of the present invention, a composition containing at least one lantibiotic is used in a medicament to treat a platelet aggregating condition caused by narrowing of the lumen, plaque formation, and or the presence of foreign bodies/medical instruments.

In other embodiments of the present invention, a composition for the treatment of membrane associated diseases and disorders as described herein can contain at least one lantibiotic is provided, wherein the lantibiotic is a Type A or a Type B lantibiotic. In another embodiment, the composition contains a Type B lantibiotic. In a further embodiment, the Type B lantibiotic can be selected from the group including duramycin, duramycin B, duramycin C, analogs of duramycin, or mixtures thereof. In further embodiment of the present invention, a composition for the treatment of membrane associated diseases or disorders not including dry eye or lung disease is provided, wherein the composition contains at least one lantibiotic or a pharmaceutically acceptable salt thereof wherein the lantibiotic is a Type A or a Type B lantibiotic. In separate embodiment of the present invention, a composition for the treatment of membrane associated diseases or disorders not including dry eye or lung disease is provided, wherein the composition contains at least one lantibiotic, wherein the lantibiotic is not duramycin.

In an additional embodiment of the present invention, a composition for the treatment of membrane-associated diseases and disorders is described, wherein the composition contains a compound of Formula I,

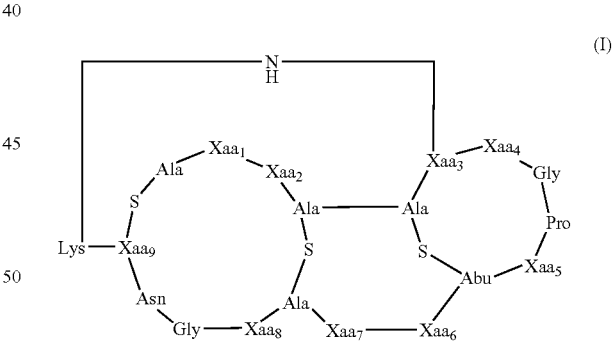

or a pharmaceutically acceptable salt thereof, wherein:

$Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine.

In a separate embodiment of the present invention, a composition for the treatment of membrane-associated diseases and disorders is disclosed, wherein the composition contains:

(a) a compound of Formula I,

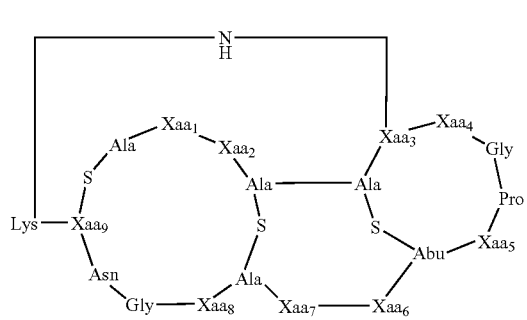
(I)

or a pharmaceutically acceptable salt thereof, wherein $Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine; and (b) a compound of Formula II,

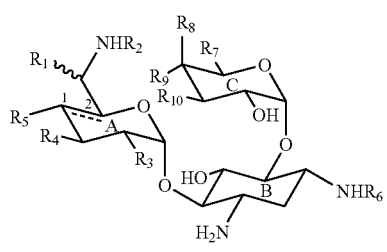
(II)

or a pharmaceutically acceptable salt thereof, wherein $R_1$, $R_2$, $R_3$, $R_4$, $R_5$, $R_6$, $R_7$, $R_8$, $R_9$, and $R_{10}$ are independently selected from the group consisting of hydrogen, amines, alcohols, alkyl alcohols, alkyl amines, substituted alkyl amines, and ketones.

In a further embodiment of the present invention, a composition for the treatment of membrane-associated diseases and disorders containing at least one lantibiotic in combination or alternation with an aminoglycoside is described; in one embodiment the lantibiotic can be a Type B lantibiotic and the aminoglycoside is tobramycin.

In a further embodiment of the present invention, a method for the treatment of membrane-associated diseases and disorders is described, the method includes the administration of a therapeutic amount of a composition containing at least one lantibiotic, wherein the lantibiotic contains a Type A lantibiotic, a Type B lantibiotic, or mixtures thereof.

In an additional embodiment of the present disclosure, a method for the treatment of membrane-associated diseases and disorders is described, the method includes administering to a patient a therapeutic amount of a composition containing a composition of Formula I,

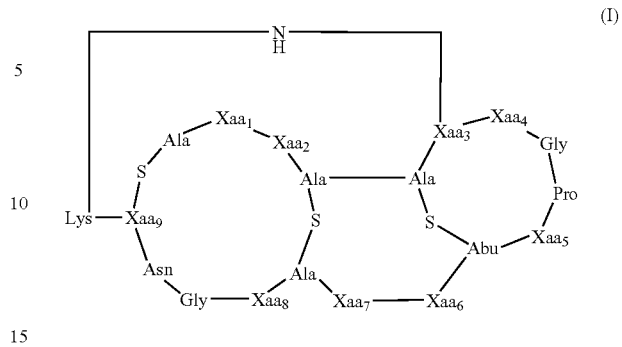
(I)

or a pharmaceutically acceptable salt thereof, wherein $Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine.

In a separate embodiment of the present invention, a method for the treatment of membrane-associated diseases and disorders is described, the method includes administering to a patient a therapeutic amount of a composition containing a compound of Formula I

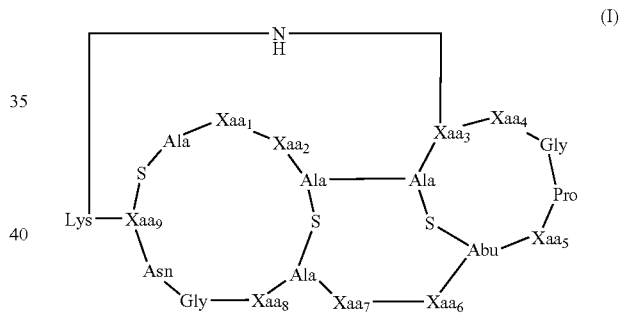
(I)

or a pharmaceutically acceptable salt thereof, wherein $Xaa_1$, $Xaa_2$, $Xaa_3$, $Xaa_4$, $Xaa_5$, $Xaa_6$, $Xaa_7$, $Xaa_8$, and $Xaa_9$ are independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine; and a compound of Formula II,

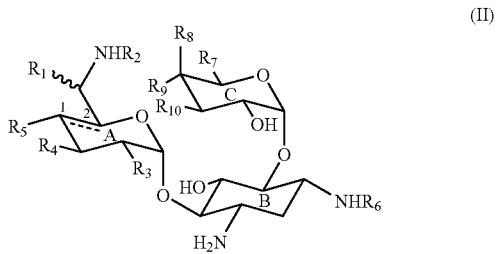
(II)

or a pharmaceutically acceptable salt thereof, wherein $R_1$, $R_2$, $R_3$, $R_4$, $R_5$, $R_6$, $R_7$, $R_8$, $R_9$, and $R_{10}$ are independently selectly from the group consisting of hydrogen, amines, alcohols, alkyl alcohols, alkyl amines, substituted alkyl amines, and ketones.

As a further embodiment of the present disclosure, a method for the treatment of membrane-associated diseases and disorders is described, the method includes administering to a patient a therapeutic amount of a composition containing a lantibiotic and an aminoglycoside, wherein the lantibiotic is duramycin and the aminoglycoside is tobramycin.

In particular, the present invention provides the following:

a) a pharmaceutical composition for the treatment of membrane-associated diseases and disorders in a subject, containing at least one lantibiotic, or a pharmaceutically acceptable salt thereof, optionally with a pharmaceutically acceptable carrier; and optionally in combination or alternation with one or more therapeutic agents;

b) a method for the treatment of membrane-associated diseases and disorders in a subject, containing administering an effective amount of a composition containing at least one lantibiotic, or a pharmaceutically acceptable salt thereof, optionally with a pharmaceutically acceptable carrier, excipient, or diluent, and optionally in combination and/or alteration with one ore more other therapeutic agents;

c) use of at least one lantibiotic compound as disclosed herein, or a pharmaceutically acceptable salt thereof, optionally with a pharmaceutically acceptable carrier or diluent, for the treatment of membrane-associated diseases and disorders, optionally in combination with one or more other therapeutic agents; and d) use of at least one lantibiotic compound as disclosed herein, or a pharmaceutically acceptable salt thereof, optionally in combination with one or more other effective therapeutic agents, and optionally with a pharmaceutically acceptable carrier or diluent, in the manufacture of a medicament for the treatment of membrane-associated diseases and disorders in a subject.

DETAILED DESCRIPTION OF THE INVENTION

The present invention provides methods and compositions useful in the treatment of membrane-associated diseases and disorders by the administration of a composition containing at least one lantibiotic. The lantibiotic can be a Type A lantibiotic or can be a Type B lantibiotic such as duramycin, duramycin B or duramycin C. Additionally, the compositions useful in the present invention for the treatment of membrane-associated diseases and disorders can optionally contain aminoglycosides.

While compositions and methods are described in terms of containing or including various components or steps, the compositions and methods can also "consist essentially of" or "consist of" the various components and steps.

I. Membrane-Associated Diseases

The present invention is directed to compositions and methods useful in the treatment of membrane-associated diseases and disorders. In one embodiment, the methods and compositions described herein can be used to treat mammals. A mammal, as a subject or patient in the present disclosure, can be from the family of Primates, Carnivora, Proboscidea, Perissodactyla, Artiodactyla, Rodentia, and Lagomorpha. Among other specific embodiments a mammal of the present invention can be *Canis familiaris* (dog), *Felis catus* (cat), *Elephas maximus* (elephant), *Equus caballus* (horse), *Sus domesticus* (pig), *Camelus dromedarious* (camel), *Cervus axis* (deer), *Giraffa camelopardalis* (giraffe), *Bos taurus* (cattle/cows), *Capra hircus* (goat), *Ovis aries* (sheep), *Mus musculus* (mouse), *Lepus brachyurus* (rabbit), *Mesocricetus auratus* (hamster), *Cavia porcellus* (guinea pig), *Meriones unguiculatus* (gerbil), or *Homo sapiens* (human). In a particular embodiement, the mammal is a human. In other embodiments, animals can be treated, the animals can be vertebrates, including both birds and mammals. Birds suitable as subjects within the confines of the present invention include *Gallus domesticus* (chicken) and *Meleagris gallopavo* (turkey).

Membrane-associated diseases and disorders suitable for treatment by the compositions and formulations of the present disclosure include but are not limited to the following: inflammation (including but not limited to arthritis), xerostomia (including but not limited to xerostomia-facilitated gingivitis), ciliary dyskinesia, and platelet aggregation. Also included as membrane-associated diseases or disorders suitable for treatment with formulations and/or compositions of the present disclosure are gastrointestinal disorders such as gastritis.

A. Inflammatory Diseases

In one embodiment of the present invention, a composition containing at least one lantibiotic is used to treat an inflammatory condition of the central nervous system. In another embodiment of the present invention, a composition containing at least one lantibiotic is used in a medicament to treat an inflammatory condition of an organ such as the kidney, liver, stomach, bladder, bowels, pancreas, thyroid, heart, or other organ. In a particular embodiment, the compositions described herein are not used to treat a disease or disorder of the lung. In another particular embodiment, the compositions described herein are not used to treat a disease or disorder of the eye.

In still another embodiment of the present invention, a composition containing at least one lantibiotic is used in a medicament to treat an inflammatory condition of the immune system, such as, but not limited to autoimmune disease.

In a different embodiment of the present invention, a composition containing at least one lantibiotic is used in a medicament to treat an inflammatory condition of the joints, such as arthritis. Types of arthritis include, but are not limited to: anklyosing spondylitis, cervical arthritis, fibromyalgia, gout, infectious arthritis, juvenile rheumatoid arthritis, lumbosacral arthritis, osteoarthritis, osteonecrosis, osteoporosis, Paget's Disease, psoriatic arthritis, Reiter's Syndrome, rheumatic diseases, rheumatoid arthritis, and/or rheumatoid foot and ankle.

In another embodiment of the present invention, a composition containing at least one lantibiotic is used in a medicament to treat an inflammatory condition of the skin. In yet another embodiment of the present invention, a composition containing at least one lantibiotic is used in a medicament to treat an inflammatory condition of the mouth, ears, nose, throat, sinuses, or that results in other upper respiratory dysfunction.

In a further embodiment of the present invention, a composition containing at least one lantibiotic is used in a medicament to treat an inflammatory condition associated with cancer. In another embodiment of the present invention, a composition containing at least one lantibiotic is used in a medicament to treat an inflammatory condition associated with an infectious agent, including but not limited to algal, bacterial, viral, rickettsial, prion, fungal, protozoan, slime molds, and parasitic infectious agents.

In an additional embodiment of the present invention, a composition containing at least one lantibiotic is used in a medicament to treat an inflammatory condition associated with a tissue that is hypersensitive to or that has been overexposed to: use, abrasion, laceration, pressure, full or partial vacuum, heat, cold, arid environment, wind, chemical irritants, antigens or allergens, toxic substances, pollution, electrical current, magnetic current, ultraviolet light, nuclear radiation, ultrasound, or other high energy radiation.

The inflammatory diseases of the Central Nervous System (CNS) include but are not limited to meningitis infections (including pyogenic, granulomatous, and lymphocytic meningitis); and parenchymal infections such as those caused by bacteria (e.g., the syphilis spirochete), viruses, fungi, parasites, and prions (scrapie, kuru, Creutzfeldt-Jakob disease, as well as cerebral abscesses (which are primarily but not exclusively bacterial in origin). In one embodiment, the compositions and formulations described herein can be used to treat cerebritis. In a further embodiment, the compositions and formulations described herein can be used to treat encephalitis and or myelitis.

More specifically, in one embodiment the formulations and compositions disclosed herein can be used to treat inflammatory diseases of the central nervous system including but not limited to the following: algal disorders including prototheocosis; bacterial disorders including abscessation and bacterial meningitis; other typically bacterial disorders including diskospondilitis and otitis media-interna; idiopathic inflammatory disorders including eosinophilic meningoenciphalitis, polioencephalomyelitis, granulomatous meningoencephalomyelitis, meningitis (including steroid responsive meningitisarteritis and other variants), miscellaneous meningitis/meningoencephalitis (including pug dog encephalitis), necrotizing encephalitis, pyogranulomatous meningoencephalomyelitis, and Shaker Dog disease; mycotic disorders including those associated with infection by *Cryptococcus neoformans, Blastomyces dermatitidis, Histoplasma capsulatum, Coccidioides immitis, Geotrichum candidum* (cerebral granulomas, choriomeningitis), *Aspergillus* sp. (cerebral granulomas), *Paecilomyces* (brain abscess or multifocal perivascular granulomas), *Filobasidiella neoformans* var. *neoformans* mating type "alpha" and others; parasitic disorders including encephalomyelitis arising from infection by *Dirofilaria immitis, Angiostrongylus vasorum, Angiostrongylus cantonensis* (which causes paraparesis and ataxia in dogs), *Dirofilaria immitis* (heartworm), *Cuterebra*, (Cuterebriasis), *Cysticercus cullosae, Toxocara canis* (the common roundworm in dogs, and visceral larva migrans syndrome in dogs and humans), *Baylisascaris* sp. (usually *procyonis*: roundworm and cerebrospinal nematodiasis), *Taenia* sp. (usually *seralis*), *Ancylostoma canium*, and *Coenurus serialis*; prion protein disorders such as spongiform encephalopathy; protozoal encephalitis-encephaloymyelitis disorders including toxoplasmosis, neosporosis, sarcocystosis, encephalitozoonosis, trypanosomiasis, acanthamebiasis, babesiosis, and leishmaniasis; rickettsial disorders including Rocky Mountain Spotted Fever, canine Ehrlichiosis, and Salmon Poisoning; viral disorders including Aujeszky's disease, Borna disease, herpes virus encephalomyelitis, canine herpes virus encephalomyelitis, canine distemper encephalomyelitis (and its variant in immature animals), multifocal distemper encephalomyelitis, old dog encephalitis, chronic relapsing encephalomyelitis, post-vaccinal canine distemper encephalitis, human immunodeficiency virus, feline immunodeficiency virus, infectious peritonitis, feline infectious peritonitis, leukemia virus, feline leukemia virus, infectious hepatitis, infectious canine hepatitis, La Crosse virus hepatitis, parvovirus encephalitis, rabies, post-vaccinal rabies, tick-borne encephalitis (including Lyme disease), and tick-borne encephalitis in dogs; fungal diseases; and non-infectious inflammatory CNS disorders such as Alzheimer's disease, Parkinson's disease, multiple sclerosis, amyotrophic lateral sclerosis (ALS, also known as Lou Gehrig's disease), myasthenia gravis, or other autoimmune diseases.

In another embodiment, methods are provided to treat organ-specific inflammatory diseases including but not limited to the following organs and disorders: kidney (e.g., glomerulonephritis); pancreas (e.g., juvenile diabetes and type I diabetes); liver (e.g., viral hepatitis); joints (e.g., adult and juvenile rheumatoid arthritis, osteoarthritis, tendonitis or bursitis, gouty arthritis, polymyalgia rheumatica, scleroderma, lupus, polymyositis, dermatomyositis, psoriatic arthritis, ankylosing spondylitis, Reiter's syndrome, joint lubrication disorders, tuberculosis arthritis, infectious arthritis (gonorrhea, also known as gonococcal arthritis), and including but not limited to disorders of the extremities, elbows, shoulders, knees, hips, back and neck); bowels (e.g., Crohn's disease, ulcerative colitis, and related conditions); immune system (e.g., allergic rhinitis (hay fever)); cardiovascular system (e.g., myocarditis, atherosclerosis and *C. pneumoniae*-mediated atherosclerosis); thyroid (e.g., thyroiditis in its acute (pyogenic or suppurative), subacute (such as granulomatous/DeQuervain's, and lymphocytic) and chronic (such as Hashimoto's/chronic lymphocytic and Riedel's invasive fibrous) forms, which are usually bacterial and gram-positive but can be associated with adenovirus, coxsackievirus, influenzae, Epstein-Barr virus, mumps, echovirus, and enterovirus, and including Grave's disease and other autoimmune diseases); gastrich or stomach (e.g., gastritis, both chronic & acute). In another embodiment, inflammatory diseases that can be treated by the compositions and formulations of the invention include but are not limited to those associated with the following parts of the anatomy: cervix (e.g., cervicitis), esophagus (e.g., esophagitis), rectum (e.g., proctitis), sclera (e.g., scleritis), sinuses (e.g., sinusitis), or skin (e.g., including psoriasis).

In still another embodiment, methods are provided to treat inflammation of the larynx, including but not limited to the following causes of inflammation: viral (including laryngotracheitis (croup), herpes simplex, cytomegalovirus, and human papillomavirus); bacterial (including supraglottitis, laryngeal abscess, gonorrhea, diphtheria) nature, leprosy, scleroma, actinomycosis, tularemia, glanders, and the spirochete syphilis); mycotic (including candidiasis, blastomycosis, histoplasmosis, coccidiomycosis, aspergillosis, and cryptococcosis); mycobacterial; parasitic (including trichinosis, leishmaniasis, schistosomiasis, cryptosporidiosis, and syngamus laryngeus); idiopathic (including sarcoidosis and Wegener's granulomatosis); spasmodic croup; traumatic laryingitis; allergic or hypersensitivity reactions such as angioedema and Stevens-Johnson syndrome; immune and idiopathic disorders (including rheumatoid arthritis, systemic lupus erythematosus, cicatricial pemphigoid, relapsing polychondritis, amyloidosis, Sjögren's syndrome (a prelymphoma syndrome), and infections of the immunocompromised host (due to AIDS, chemotherapy, chronic corticosteroid therapy, or immunosuppression for transplantation)); inhalation laryngitis (including acute (thermal) injury, pollution and inhalant allergy, and carcinogens); radiation injury such as radiation laryngitis and radionecrosis; and vocal abuse and vocal misuse syndromes (including vocal-cord hemorrhage, muscle tension dysphonias, and contact ulcer and granuloma).

In a further embodiment the formulations and compositions of the present invention can be used to treat inflammatory diseases of the ear or of the skin in other affected parts of the body, wherein the diseases include but are not limited to: otis media (inflammation and/or infection of the middle ear); otis externa ("swimmers ear" and other inflammations of the external auditory canal); allergic dermatitis; contact dermatitis; seborrheic dermatitis; neurodermatitis; psoriasis; irritant contact dermatitis; dermatophytosis; infectious eczematoid dermatitis; discoid lupus erythematosus; angiolymphoid hyperplasia; lupus erythematosus and other autoimmune disorders; porphyria; phototoxic dermatitis; cellulites of the pinna; infectious perichondritis; trauma; insect bite; sunburn; frostbite; Cogan syndrome; vasculitides; leprosy; chondrodermatitis nodularis helices; radiodermatitis; Darier disease; granuloma faciale; granuloma annulare; angiolymphoid hyperplasia with eosinophilia and Kimura disease; juvenile spring eruption of the ears.

In an additional embodiment the formulations and compositions of the present invention can be used to treat inflammatory diseases of the mouth including, but not limited to, gingivitis.

In a further embodiment the formulations and compositions of the present invention can be used to treat cancer-related inflammatory disorders observed where the disease is suspected to have a viral or bacterial origin, including but not limited to infections by *H. pylori* (gastric ulcers and gastric cancer) and viral infections associated with hepatitis B, hepatitis C, and human papillomavirus, as well as cancer-related inflammatory disorders from other origins, such as cutaneous myoepithelioma.

The compositions and formulations of the present invention are suitable for treating numerous specific membrane-associated inflammatory diseases and disorders, in human patients as well as in animal patients. These medical conditions include but are not limited to those listed herein. A more complete listing of membrane-associated diseases and disorders which are contemplated by the present invention, as well as the details of the morphology of such diseases, can be found in Schaeffer, R. J., *J Urology* 171: pp. 1745-1765 (2004); Cotran, R. S., et al., "Robins Pathologic Basis of Disease", W.B. Saunders, 1999; Underwood, J., "General and Systematic Pathology, $4^{th}$ Edition", Churchill Livingstone, 2004; and on the National Institute of Health Internet website (www.nlm.nih.gov).

The lists of diseases and disorders provided above are non-exclusive. The invention formulations are contemplated for use to treat these and other inflammatory diseases and disorders and their variants, in particular, where they occur outside the lung and the eye, whether in human or animal patients.

B. Xerostomia

In one embodiment of the present invention, a composition containing at least one lantibiotic is used in a medicament to treat xerostomia. In another embodiment of the present invention, a composition containing at least one lantibiotic is used in a medicament to treat drug-induced xerostomia. In an alternative embodiment of the present invention, a composition containing at least one lantibiotic is used in a medicament to treat a condition of xerostomia caused by another class of medications, including but not limited to anticholinergics, antispasmodics, antihypertensives, antidepressants, anticonvulsants, pain killers, anti-rejection drugs, anti-pyschotics, decongestants, and antihistamines.

In a further embodiment of the present invention, a composition containing at least one lantibiotic is used in combination with a xerostomia-inducing second drug to mitigate the xerostomic effects of the second drug. In still another embodiment of the present invention, a composition containing at least one lantibiotic is used in a medicament to treat xerostomia associated with elevated stress, anxiety, or depression. In another embodiment of the present invention, a composition containing at least one lantibiotic is used in a medicament to treat xerostomia associated with an endocrine disease or autoimmune disorder. In a further embodiment of the present invention, a composition containing at least one lantibiotic is used in a medicament to treat xerostomia associated with destruction of the glands by radiation therapy to the neck, traumatic injury to the neck, neck surgery, or by other direct injury to the glands or their controlling autonomic nerves. In a particular embodiment of the present invention, a composition containing at least one lantibiotic is used in a medicament to treat geriatric xerostomia.

Thus in an embodiment of the invention, methods are provided to treat xerostomia, including but not limited to the following: xerostomia associated with xerostomia-producing drugs (such as anticholinergics, antispasmodics, antihypertensives, antidepressants, anticonvulsants, pain killers, anti-rejection drugs, and antipsychotics, as well as over-the-counter decongestants and antihistamines, and chemotherapy); xerostomia associated with states of elevated stress, anxiety, depression, certain endocrine diseases such as hypothyroidism, and auto-immune disorders such as Sjögren's syndrome; xerostomia associated with destruction of the glands by radiation therapy to the neck, traumatic injury to the neck, neck surgery, or by other direct injury of the glands or their controlling autonomic nerves; and xerostomia associated with advanced age.

C. Ciliary Dyskinesia

In one embodiment of the present invention, a composition containing at least one lantibiotic is used in a medicament to treat primary or secondary ciliary dyskinesia.

In a further embodiment of the present invention, a composition containing at least one lantibiotic is used in a medicament to treat a condition of primary ciliary dyskinesia that affects the mouth, ears, nose, throat, sinuses, upper airways, or results in other upper respiratory effects.

In another embodiment of the present invention, a composition containing at least one lantibiotic is used in a medicament to promote mucociliary clearance of retained mucus secretions from the genito-urinary tract, spermatozoa, ovaries, or fallopian tubes.

In still another embodiment of the present invention, a composition containing at least one lantibiotic is used in a medicament to promote mucociliary clearance of the neutrophils or macrophages of a patient.

In an additional embodiment of the present invention, a composition containing at least one lantibiotic is used in a medicament to treat a condition of infertility associated with primary ciliary dyskinesia. In one embodiment, the infertility is male. In another embodiment, the infertility is female.

In a further embodiment of the present invention, a composition containing at least one lantibiotic is used in a medicament to promote mucosal hydration in the upper respiratory tract or genito-urinary tract. In one embodiment, a composition containing at least one lantibiotic is used in a medicament to treat vaginal dryness and or promote vaginal secretions.

In an alternative embodiment of the present invention, a composition containing at least one lantibiotic is used in a medicament to treat hydrocephalus caused by ciliary malfunction.

In another embodiment of the present invention, a composition containing at least one lantibiotic is used in a medicament to treat or prevent embryonic situs inversus (dextrocardia) or Kartagener's syndrome.

In yet another embodiment of the present invention, a composition containing at least one lantibiotic is used in a medicament to treat or prevent ciliary dyskinesia in the upper respiratory tract caused by a viral or bacterial respiratory infection, smoking, air pollution, chemical or thermal burns to the airways, intubation and mechanical ventilation, and near-drowning.

In a further embodiment of the present invention, a composition containing at least one lantibiotic is used in a medicament to treat or prevent ciliary dyskinesia in the upper respiratory tract caused by influenza, adult respiratory distress syndrome, or ventilator-associated pneumonia.

The lantibiotics of the present invention can be capable of stimulating the ciliary beat frequency in a subject in need of such treatment. The present invention thus includes a method of treating ciliary dyskinesia. The method comprises the steps of administering to the subject a compound containing a lantibiotic, or pharmaceutically acceptable salt thereof, in a pharmaceutical carrier having an amount of said compound effective to increase ciliary beat frequency in the affected part of the body.

Embodiments of the invention provide a method to treat a patient having inadequate ciliary beat frequency for any reason, including but not limited to patients who suffer from: inadequate mucociliary clearance of retained secretions in the sinuses, upper airway, or middle or inner ears; primary ciliary dyskinesia; secondary ciliary dyskinesia caused by a viral or bacterial respiratory infection, smoking, air pollution, chemical or thermal burns to the airways; secondary ciliary dyskinesia caused by intubation and mechanical ventilation, or near-drowning; secondary ciliary dyskinesia caused by influenza, adult respiratory distress syndrome, or ventilator-associated pneumonia; embryonic situs inversus (dextrocardia); Kartagener's syndrome; otitis media; upper respiratory infection; diseases involving dysfunction of the genito-urinary mucociliary clearance defense system caused by impairment of ciliary movement; diseases of the immune system caused by impairment of ciliary movement of neutrophils and macrophages; hydrocephalus caused by impairment of ciliary movement; male infertility caused by impairment of the ciliary propulsion of the spermatozoa; female infertility caused by impairment of ciliary movement on the luminal epithelial cells of the ovaries or fallopian tubes, and any other disease caused by an impairment of ciliary movement.

In another embodiment, in patients whose cilia are permanently incapable of any movement regardless of treatment, the active compounds of the present invention can be used to facilitate the clearance of retained mucous secretions by increasing the secretion of water into the periciliary liquid layer and by increasing the secretion of mucins by goblet cells.

The present invention thus provides methods to treat a variety of clinical manifestations of ciliary dyskinesia, such as, but not limited to absent or impaired mucociliary clearance in the respiratory and middle/inner ear tract, impaired propulsion of spermatozoa, and impaired motility of neutrophils and macrophages.

D. Platelet Aggregating Disorders

In one embodiment of the present invention, a composition containing at least one lantibiotic is used in a medicament to treat a platelet aggregation disorder. In an alternative embodiment of the present invention, a composition containing at least one lantibiotic is used in a medicament to treat or prevent at least one of the following platelet aggregating diseases: atherosclerotic cardiovascular disease, coronary artery disease, cerebral vascular disease, kidney disease, abdominal vascular insufficiency, and peripheral vascular disease. In an additional embodiment of the present invention, a composition containing at least one lantibiotic is used in a medicament to treat a platelet aggregating condition caused by narrowing of the lumen, plaque formation, and or the presence of foreign bodies/medical instruments.

In another embodiment of the present invention, a composition containing at least one lantibiotic is used in a medicament to treat or prevent atherosclerotic cardiovascular disease, or the effects associated with that disease such as aortic aneurysm or aortic embolism, sudden occlusion of an artery vessel, and or progressive narrowing of the arterial lumen.

In a further embodiment of the present invention, a composition containing at least one lantibiotic is used in treatment to mitigate the risk factors that arise from smoking, hypertension, diabetes mellitus, cholesterol abnormalities, and or homocysteinuria.

In still another embodiment of the present invention, a composition containing at least one lantibiotic is used in a medicament to treat or prevent coronary artery disease or the effects associated with that disease such as angina, unstable angina, myocardial infarction, and or sudden death.

In an alternative embodiment of the present invention, a composition containing at least one lantibiotic is used in a medicament to treat or prevent cerebral vascular disease or the effects associated with that disease such as neural deterioration, transient ischemic attack, seizures, and or cerebral vascular accident.

In an additional embodiment of the present invention, a composition containing at least one lantibiotic is used in a medicament to treat or prevent kidney disease or the effects associated with that disease such as hypertension, renal infarction and or renal failure.

In a further embodiment of the present invention, a composition containing at least one lantibiotic is used in a medicament to treat or prevent abdominal vascular insufficiency or the effects associated with that disease such as abdominal angina and bowel infarction.

In yet another embodiment of the present invention, a composition containing at least one lantibiotic is used in a medicament to treat or prevent peripheral vascular disease or the effects associated with that disease such as intermittent claudication and gangrene, or to prevent the need for amputation.

Platelet aggregating disorders are responsible for demographically important, often fatal conditions as follows. Atherosclerotic cardiovascular disease (ASCVD) damages the artery walls throughout the body and forms thrombosis, with risk factors of smoking, hypertension, diabetes mellitus, cholesterol abnormalities and homocysteinuria. In the largest arteries (the aorta), this can include aortic aneurysm or embolism; in medium and small arteries this can include sudden occlusion of the vessel and progressive narrowing of the arterial lumen. Coronary artery disease (CAD) can include angina, unstable angina, myocardial infarction (MI) and sudden death. Cerebral vascular disease (CVD) effects include progressive neural deterioration, transient ischemic attack (TIA), seizures, and cerebral vascular accident (CVA), i.e., stroke. Kidney effects include hypertension, renal infarction and renal failure. Abdominal vascular insufficiency results in abdominal angina and bowel infarction. Peripheral vascular disease (PVD) effects include intermittent claudication, gangrene and amputation. Platelet aggregating conditions are often caused by narrowing of the lumen, plaque formation, and the presence of foreign bodies/medical instruments.

II. Compounds

Duramycin is a polypeptide lantibiotic, characterized by the presence of rings formed by two unusual double-headed amino acid that contain thioether bridges, which enhances chloride secretion in airway epithelium and has been used in studies of cystic fibrosis (CF) (see, Cloutier, M. M., et al., *Am. J. Physiol*. 259, C450 (1990); Nakamura, S.; Racker, E., *Biochemistry* 23, 385 (1984); Twomey, D., et al., *Antonie van Leeuwenhoek* 82: 165-185 (2002)). Duramycin has also been shown to inhibit clatharin-coated vesicle acidification, inhibiting up to 50% of the proton translocation facilitated by chloride translocation (Stone, D. K., et al., *J. Biol. Chem*. 259: 2701-2703 (1984)).

U.S. Publication No. 2004/0147440 to Thorpe et al. describes the use of duramycin as a cell targeting molecule and teach the attachment of therapeutic molecules to the duramycin for tumor vascular targeting, imaging and treatment. Thorpe et al. take advantage of the ability of duramycin to bind to phosphatidylethanolamine, which allows it to act as a tumor targeting agent.

Lantibiotics such as duramycin have also been shown to facilitate the clearance of retained pulmonary secretions from the lungs. U.S. Pat. Nos. 5,512,269; 5,651,957; 5,683,675; and 5,716,931 to Molichem Medicines, Inc. describe methods of administering lantiobiotics, such as duramycin, to the lungs of a subject to treat cystic fibrosis, chronic bronchitis, asthma and tuberculosis.

Recently, Molina et al. discovered that lantibiotics can be used in the treatment of dry eye disease. PCT publication No. WO 2004/037167 to Molichem Medicines, Inc., published May 6, 2004, describes methods for the treatment of dry eye disease, such as keratoconjunctivitus, with a lantibiotic, such as duramycin (as shown in Example 2 of WO 2004/037167).

Lantibiotics are antibiotic peptides distinguished by the presence of the rare thioether amino acids lanthionine and/or methyllanthionine. They are produced by Gram-positive bacteria as gene-encoded precursor peptides and undergo post-translational modification to generate the mature peptide. The structural gene for the prepeptide and the genes involved in biosynthesis, processing, export as well as regulation and producer strain self-protection are organized in clusters. Based on their structural and functional features lantibiotics are currently divided into two major groups—type A and type B lantibiotics. The flexible amphiphilic type-A lantibiotics act primarily by pore formation in the bacterial membrane, a mechanism which was recently shown, e.g. for nisin and epidermin, to involve the interaction with specific docking molecules such as the membrane precursor lipid II. The rather rigid and globular type-B lantibiotics inhibit enzyme functions through interaction with the respective substrates: mersacidin and actagardine inhibit the cell wall biosynthesis by complexing lipid II, whereas the cinnamycin-like peptides inhibit phospholipases by binding phosphoethanolamine (Hoffman, A., et al., *Il Farmaco*, 57: pp. 685-691 (2001); Pag, U., et al., *Current Pharm. Design*, 8: pp. 815-833 (2002)).

Lantibiotics are defined as bacterium-derived ribosomally synthesized lanthionine-containing peptides with antibiotic activity (Jack, et al., 1995, *Microbiol. Rev*. 59:171-200; Bierbaum et al., 1993, *Zentralbl. Bakteriol*. 278:1-22; Jack, et al., 1995, *Trends Biotechnol*. 13:269-278). They generally contain unsaturated amino acids such as 2,3-didehydroalanine (dhA or U) (2)-2,3-didehydrobutyrine (dhB or O), and 2-aminobutyric acid (Abu). The lantibiotics are divided into two types—Type A and Type B (Jung, 1991, in: Nisin and Novel Lantibiotics., Jung, et al., eds., pp. 1-34. ESCOM Science, Leiden). A further subtype, Type C lantibiotics (the so-called LanC proteins), has also been more recently classified based on more detailed understandings of the previous two classifications (Kupke, T., et al., J. Bacteriol., 178: pp. 1335-1340 (1996)). Type A contains screw-shaped, amphipathic molecules with molecular masses between 2151 and 4635 Da and with 2 to 7 net positive charges. Type B consists of more globular molecules with molecular masses between 1825 and 2042 Da and with either no net charge or a net negative charge. They usually contain a higher proportion of modified amino acid residues than type A.

Lantibiotics suitable for use with the present invention include type A, type B and type C lantibiotics, as well as synthetic and natural analogues thereof, and combinations of such lantibiotics. Type A lantibiotics suitable for use with the present invention include but are not limited to nisin, subtilin, epidermin, gallidermin, Pep5, mersacidin, actagardine, and combinations thereof. Type B lantibiotics suitable for use with the present invention include but are not limited to anocovenin, cinnamycin (also known as Ro 09-0198 and lanthiopeptin), duramycin (McNulty, et al., *Xenobiotica*, 33, pp. 197-210 (2003)), also known as leucopeptin, duramycin B, duramycin C, ancovenin, synthetic analogues thereof, and mixtures thereof. In a particular embodiment, the lantibiotic is a Type B lantibiotic, or structural analogue of a Type B lantibiotic. A lantibiotic suitable for use with the present invention is a lantibiotic of Formula I,

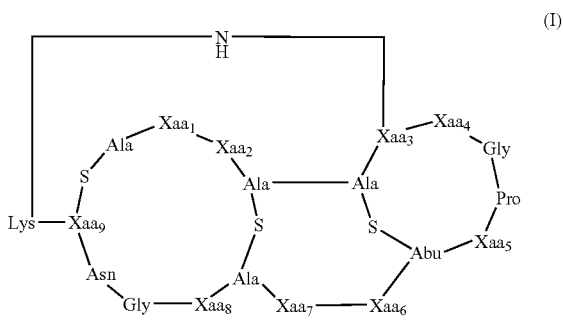

(I)

wherein Xaa$_1$, Xaa$_2$, Xaa$_3$, Xaa$_4$, Xaa$_5$, Xaa$_6$, Xaa$_7$, Xaa$_8$, and Xaa$_9$ are independently selected from the group of amino acids (both naturally occurring and synthetic) consisting of but not limited to 2-aminoadipic acid (Aad), aminobutyric acid (Abu), aminobenzoic acid (Abz), aminocyclohexanoic acid (Ac6c), aminocyclopentanoic acid (Ac5c), aminocyclopropanoic acid (Ac3c), aminodecanoic acid (Adc), aminododecanoic acid (Ado), aminohexanoic acid (Ahx), aminoisobutyric acid (Aib), alanine (Ala), alloisoleucine (AIle), allothreonine (aThr), aminomethylbenzoic acid (Amb), aminomethylcyclohexanoic acid (Amc), 2-amino-2-thiazolidine-4-carboxylic acid, aminononanoic acid, aminooctanoic acid, aminopentanoic acid (Avl), arginine (Arg), asparagine (Asn), aspartic acid (Asp), aminoundecanoic acid, aminovaleric acid, biphenylalanine, benzoylphenylalanine, carnitine, 4-cyano-2-aminobutyric acid, 3-cyano-2-aminopropionic acid, cyclohexylalanine, cyclohexylglycine, citruline (Cit), cysteine (Cys), cystine, 2,4-diaminobutyric acid (A2bu), 2,3-diaminopropionic acid (A2pr), diethylglycine, dihydrotryptophan, diaminobenzoic acid, dipropylglycine, 2,3-diaminopropionic acid, 2,3-didehydroalanine (Dha), (Z)-2,3-didehydroaminobutyric acid (Dhb), erythro-3-hydroxyaspartic acid (HyAsp), 2-aminobutyric acid (Abu), dolaproine (Dap), dolaisoluine (Dil), dolaisovaline (Dov), Hiv, methyl valine (MeVal), 3-amino-6-octyneoic acid (Doy), dolaphenine (Doe), dolahexanoic acid (Dhex) 2-methyl-3-aminoisocaproic acid (Dml, dolamethylleuine), 2-amino-4-phenylisovaleric acid (Dpv, dolaphenvaline), diethylglycine, dihydrotryptophan, gamma-carboxyglutamic acid, glutamine (Gln), glutamic acid (Glu), glycine (Gly), histidine (His), homoarginine, homocysteine (Hcy), homophenylalanine, homoserine (Hse), homoserinelactone (Hsl), homotyrosine, hydroxylysine (Hyl), hydroxyproline (Hyp), 2-indolinecarboxylic acid, 2-indanylglycine, isoglutamine (iGln), isoleucine (Ile), indoleglycine, isonipecotic acid, isovaline (Iva), leucine (Leu), lysine (Lys), β-mercapto-β,β-cyclopentamethylenepropanoic acid, methionine (Met), methionine S-oxide (Met(O)), muramicacid (Mur), napthylalanine, neuraminicacid (Neu), norleucine (Nle), norvaline (Nva), octahydroindolecarboxylic acid, ornithine (Om), pyridylalanine, penicillamine, pyroglutamic acid, phenylalanine (Phe), phenylglycine, phosphoserine (Ser(P)), pipecolic acid, 4-phosphomethylphenylalanine, propargylglycine, proline (Pro), putrescine, sarcosine (Sar), serine (Ser), statine (Sta), statine analogs, taurine (Tau), thiazolidinecarboxylic acid, tetrahydroisoquinoline-3-carboxylic acid, tert-leucine, threonine (Thr), thyroxine (Thx), tryptophan (Trp), tyrosine (Tyr), 3,5-diiodotyrosine (Tyr(I$_2$)), valine (Val) and aminoethyloxy-ethyloxyacetic acid (AEEA). Abbreviations for amino acids, as used herein, are in accordance with the IUPAC guidelines on nomenclature (Nomenclature and Symbolism for Amino Acids and Peptides. *Eur. J. Biochem.* 138: pp. 9-37(1984)).

Xaa$_1$-Xaa$_9$ can be independently selected from natural or synthetic amino acids, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and β-methyllanthionine. In a particular embodiment, the lantibiotics used in the compositions of the present invention can be selected from the group consisting of duramycin, duramycin B, duramycin C, structural analogs of duramycin, or a combination thereof. In another embodiment the lantibiotic is duramycin.

The lantibiotics suitable for use with the present invention can be obtained by isolation from naturally occurring bacterium using known techniques such as fermentation, obtained from commercial sources, produced by genetic engineering techniques, or synthesized using known synthetic chemistry techniques.

In the event that the lantibiotic or lantibiotics of the present invention are prepared by synthetic routes, the amino acids used within the present invention can be obtained from a commercial source (e.g., Advanced ChemTech, Inc., Louisville, Ky.; CalBioChem, CA; and, Kyowa Hakko Kogyo Co., LTD., Tokyo, Japan), by fermentation methods, or can be prepared synthetically using any number of techniques in the art, e.g. through the displacement reactions on α-halo acids. The amino acids used within the present invention can be α-amino acids in L-(levorotatory), D-(dextrorotatory), or R-(racemic) stereochemistry, and can include glycine, which does not have optical isomers, and/or can include β-amino acids. Similarly, the lantibiotics of the present invention can also be prepared by biomimetic synthetic means, such as those described by Burrage, S., et al. (*Chem. Eur. J.*, 6: pp. 1455-1466 (2000)). Individual stereoisomers can be obtained commercially, or by methods known in the art, such as the separation of stereoisomers in chiral chromatographic columns.

Further, the lantibiotic compounds of the present invention, especially those of Formula I, can exist in unsolvated as well as solvated forms with pharmaceutically-acceptable solvents such as water, ethanol, and the like. In general, solvated forms of the lantibiotic compounds are considered to be equivalent to the unsolvated forms for the purposes of the present invention.

The isolation of lantibiotics from naturally occurring bacteria includes production and isolation from a variety of known producing strains using known procedures, as well as those techniques described, for example, by Hayashi, et al., (*J. Antibiotics*, 43: pp. 1421-1426; (1990)), Pridham, et al. (*Phytopathology*, 46, pp. 575-581 (1956)), Shotwell, et al. (*J. Am. Chem. Soc.*, 80: pp. 3912-3914 (1958)), and Nakamura, et al. (*Biochemistry*, 23: pp. 385-389 (1984)). Synthetic chemistry techniques include combinatorial chemistry, automated techniques, and the like, such as those described by Bodansky (*Principles of Peptide Synthesis*, 2$^{nd}$ Ed., Springer-Verlag, 1993). Genetic engineering techniques include recombinant techniques based on modified Gram-positive and Gram-negative bacteria, such as those techniques described by Widdick et al. (Proceedings of the National Academy of Science, USA, Vol. 100, no. 7, pp. 4316-4321; (2003)), and by Sahl ("Gene-Encoded Antibiotics Made in Bacteria", in *Antimicrobial Peptides: Symposium No.* 186 by Ciba Foundation Symposium, pp. 27-53; (1996)).

Synthesis of lantibiotics for use in the present invention can employ nucleic acid sequences isolated from *S. cinnamoneus* which encode for duramycin or fragments thereof. The nucleic acid sequences can encode for preduramycin, produramycin, the preduramycin leader sequence, or fragments thereof. Alternatively peptides encoded by the duramycin gene and vectors and host cells containing the nucleic acid sequences encoding these peptides can be used, which include, preduramycin, produramycin, the preduramycin leader and derivatives thereof. Such peptides can be isolated and/or purified in accordance with known techniques. In particular, one can introduce into a suitable host cell a nucleic acid sequence encoding preduramycin or produramycin, culturing said cell under suitable conditions to produce such peptides, and isolating preduramycin, produramycin or mature duramycin produced by said cell. The host cell can be a gram-positive bacterium, such as from the genus *Bacillus, Streptomyces* or *Streptococcus*. Such techniques and nucleotide sequences are further described in PCT Publication No, WO 04/033706 to Molichem Medicines, Inc.

In accordance with the present invention, lantibiotics suitable for use in the present invention can also be obtained by fermentation of bacteria of a variety of classes. Such suitable bacteria include but are not limited to Lactic acid bacteria, Streptococcal bacteria, Streptoverticillium bacteria, Micrococcal bacteria, Ruminococcal bacteria, *Bacillus* species, Enterococcal bacteria, *Actinoplanes* species of bacteria, and Carnobacteria.

Examples of bacterial strains suitable for use in the fermentation of lantibiotics useful in the present invention include, but are not limited to, *Streptococcus mutans*, *salivarius*, *pyogenes*, *grisoluteus*, and *epidermis*; *Streptoverticillium cinnamoneum*, ssp. *Azacolutum*; *micrococcus varians*; *Bacillus subtilis*; *Staphylococcus epidermis*, *Staphylococcus gallinarum*, *Staphylococcus cohnil*, and *Staphylococcus warneri*; lactobacteria, including *lactobacillus*, such as *lactobacillus plantarum*, and *lactococcus*, such as *lactococcus lactis* spp.; *Actinoplanes liguriae*; *Enterococcus faecalis*; *Ruminococcus gnavus*; and *Carnobacterium piscicola*.

According to a further aspect of the present invention, combinations of lantibiotics with other known compounds are provided, for the purpose of treating membrane-associated diseases and/or membrane-associated conditions. For example, it is envisioned that lantibiotics such as duramycin can be combined or alternated with aminoglycosides, resulting in improved treatments of membrane-associated diseases or disorders. As a further example, it is envisioned that lantibiotics such as duramycin can be combined or alternated with aminoglycosides and/or therapeutic or prophylactic proteins, resulting in compositions useful in the treatment of membrane-associated diseases or disorders.

Aminoglycosides suitable for use with the present invention in preparing compositions and formulations suitable for use in the treatment of membrane-associated diseases and disorders include those bactericidal antbiotics known in the art that are generally classified as protein synthesis inhibitors that interfere with ribosomal function. Suitable aminoglycosides include but are not limited to streptomycin, neomycin, kanamycin, gentamicins such as gentamicin $C_1$, gentamicin $C_2$, and gentamycin $C_{1a}$, tobramycin, amikacin, butirosin and butirosin A, sisomicin, paromomycin, and netilmicin, as well as structurally modified analogues of such aminoglycosides. Aminoglycosides suitable for use with the present invention include those of Formula (II),

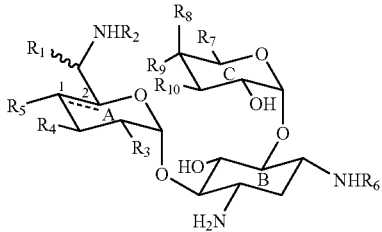

(II)

wherein the dotted line in the chemical structure indicates either a double or single bond such that the double bond does not over-extend the valence of the element (i.e. to give pentavalent carbons) and, in the case of a single bond, the valence is completed with hydrogen; and, wherein $R_1$, $R_2$, $R_3$, $R_4$, $R_5$, $R_6$, $R_7$, $R_8$, $R_9$, and $R_{10}$ are independently selected from the group consisting of hydrogen, amines, alcohols, alkyl alcohols, alkyl amines, substituted alkyl amines, and ketones. In one embodiment, $R_1$-$R_{10}$ are independently selected from the group consisting of methyl ($CH_3$), hydrogen (H), hydroxyl (OH), primary amine ($NH_2$), methyl amine (NH—$CH_3$), and methyl alcohol ($CH_2$—OH). In a particular embodiment, $R_1$, $R_2$, $R_4$, $R_5$, $R_6$, $R_8$ and $R_9$ are hydrogen, $R_3$ and $R_{10}$ are a primary amine ($NH_2$), and $R_7$ is methyl alcohol ($CH_2$—OH), such that the aminoglycoside of Formula II is tobramycin.

Tobramycin [O-3-amino-3-deoxy-α-D-glucopyranosyl-(1→4)—O-[2,6-diamino-2,3,6-trideoxy-α-D-ribo-hexopyranosyl-(1-'6)]-2-deoxy-L-streptamine], is a known antibiotic drug. See, for example, The Merck Index, Twelfth Edition, page 1619. Inhaled tobramycin was recently approved by the FDA in a 300 mg formulation for inhalation. The new product, manufactured by PathoGenesis Corporation, is referred to as TOBI™ and is indicated for cystic fibrosis patients with *Pseudomonas aeruginosa*. Both TOBI™, as well as Nebcin (tobramycin sulfate) and related salts and compounds are suitable for use in formulation of the present invention. Examples of analogs of tobramycin suitable for use in compositions of the present invention have recently been described by Hanessian, S., et al. (*Tetrahedron*, 59: pp. 983-993 (2003)), all of which (including variants with ethers, ether-linked basic moieties, amino-containing sides chains, and guanidine-containing side chains) are envisioned as being suitable for use herein. The concentration of tobramycin in the solution compositions of the present invention can generally be about 50 wt. % or less. In one embodiment for topically administrable ophthalmic compositions, the concentration of tobramycin in accordance with the present invention is about 30 wt. %.

As a further alternative formulation composition of the present invention, the formulation can contain a lantibiotic or combination of lantibiotics, an aminoglycoside, and a therapeutic or prophylactic protein or other biologically active compound or drug. In one embodiment, such a formulation can contain a lantibiotic of Formula I, an aminoglycoside of Formula II, and a therapeutic or prophylactic protein or biologically active compound or drug. In a further embodiment, a formulation for use in the treatment of membrane-associated diseases and disorders, in accordance with one aspect of the present invention, contains a duramycin lantibiotic, tobramycin, and a therapeutic protein or other biologically active compound.

Examples of therapeutic or prophylactic proteins and other biologically active drugs or compounds suitable for use in formulations of the present invention include but are not limited to hormones, antibodies, inhibitors, growth factors, trophic factors, cytokines, lymphokines, toxoids, erythropoietin, Factor VIII, insulin, amylin, tPA (tissue plasminogen activator), dornase-α, α-1-antitripsin, human growth hormones, nerve growth hormones, bone morphogenic proteins, urease, toxoids, fertility hormones, FSH (follicle stimulating hormone), LSH (lutropin-choriogonadotropic hormone), postridical hormones, tetanus toxoid, diptheria toxoid, vitamins and nutrients. In one embodiment, the therapeutic or prophylactic protein is dornase-α (Pulmozyme®, from Genentech, San Francisco, Calif.), a recombinant human deoxyribonuclease I (rhDNase).

Definitions

The terms "$C_1$-$C_{10}$ alkyl", "$C_2$-$C_{10}$ alkenyl", $C_1$-$C_{10}$ alkoxy, $C_2$-$C_{10}$ alkeno $C_2$-$C_{10}$ alkynyl, and $C_2$-$C_{10}$ alkynoxy are considered to include, independently, each member of the group, such that, for example, $C_1$-$C_{10}$ alkyl includes straight, branched and where appropriate cyclic $C_1$, $C_2$, $C_3$, $C_4$, $C_5$, $C_6$, $C_7$, $C_8$, $C_9$ and $C_{10}$ alkyl functionalities; $C_2$-$C_{10}$ alkenyl includes straight, branched, and where appropriate cyclic $C_2$, $C_3$, $C_4$, $C_5$, $C_6$, $C_7$, $C_8$, $C_9$ and $C_{10}$ alkenyl functionalities; $C_1$-$C_{10}$ alkoxy includes straight, branched, and where appropriate cyclic $C_1$, $C_2$, $C_3$, $C_4$, $C_5$, $C_6$, $C_7$, $C_8$, $C_9$ and $C_{10}$ alkoxy functionalities; $C_2$-$C_{10}$ alkenoxy includes straight, branched, and where appropriate cyclic $C_2$, $C_3$, $C_4$, $C_5$, $C_6$, $C_7$, $C_8$, $C_9$ and $C_{10}$ alkenoxy functionalities; $C_2$-$C_{10}$ alkynyl includes straight, branched and where appropriate cyclic $C_1$, $C_2$, $C_3$, $C_4$, $C_5$, $C_6$, $C_7$, $C_8$, $C_9$ and $C_{10}$ alkynyl functionalities; and $C_2$-$C_{10}$ alkynoxy includes straight, branched, and where appropriate cyclic $C_2$, $C_3$, $C_4$, $C_5$, $C_6$, $C_7$, $C_8$, $C_9$ and $C_{10}$ alkynoxy functionalities.

The term "alkyl", alone or in combination, means an acyclic, saturated straight, branched, or cyclic, primary, secondary, or tertiary hydrocarbon, including those containing from 1 to 10 carbon atoms or from 1 to 6 carbon atoms. Said alkyl radicals may be optionally substituted with groups including but not limited to methyl, ethyl, propyl, isopropyl, cyclopropyl, butyl, isobutyl, t-butyl, sec-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, heptyl, octyl; nonyl, decyl, trifluoromethyl and difluoromethyl. Moieties with which the alkyl group can be substituted include, for example, alkyl, hydroxyl, halo, nitro, cyano, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that preferably does not inhibit the pharmacological activity of the compound, either unprotected, or protected as necessary, as known to those skilled in the art, for example, as taught in Greene, et al., *Protective Groups in Organic Synthesis*, John Wiley and Sons, Third Edition, 1999, hereby incorporated by reference.

The term "alkenyl", alone or in combination, means an acyclic, straight, branched, or cyclic, primary, secondary, or tertiary hydrocarbon, including those containing from 2 to 10 carbon atoms or from 2 to 6 carbon atoms, wherein the substituent contains at least one carbon-carbon double bond. These alkenyl radicals may be optionally substituted. Examples of such radicals include but are not limited to are ethylene, methylethylene, and isopropylidene.

The term "alkynyl" means an unsaturated, acyclic hydrocarbon radical, linear or branched, in so much as it contains one or more triple bonds, including such radicals containing about 2 to 10 carbon atoms or having from 2 to 6 carbon atoms. The alkynyl radicals may be optionally substituted. Examples of suitable alkynyl radicals include but are not limited to ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like.

The terms "alkoxy" and "alkoxyalkyl" embrace linear or branched oxy-containing radicals each having alkyl portions of, for example, from one to about ten carbon atoms, including the methoxy, ethoxy, propoxy, and butoxy radicals. The term "alkoxyalkyl" also embraces alkyl radicals having one or more alkoxy radicals attached to the alkyl radical, that is, to form monoalkoxyalkyl and dialkoxyalkyl radicals. Other alkoxy radicals are "lower alkoxy" radicals having one to six carbon atoms. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" includes "monoalkylamino" and "dialkylamino" radicals containing one or two alkyl radicals, respectively, attached to an amino radical. The terms "arylamino" denotes "monoarylamino" and "diarylamino" containing one or two aryl radicals, respectively, attached to an amino radical. The term "aralkylamino", embraces aralkyl radicals attached to an amino radical, and denotes "monoaralkylamino" and "diaralkylamino" containing one or two aralkyl radicals, respectively, attached to an amino radical. The term aralkylamino further includes "monoaralkyl monoalkylamino" containing one aralkyl radical and one alkyl radical attached to an amino radical.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "alkylthio" and "arylthio" are defined as—SR, wherein R is alkyl or aryl, respectively.

The term "alkylsulfinyl" is defined as $R-SO_2$, wherein R is alkyl.

The term "alkylsulfonyl" is defined as $R-SO_3$, wherein R is alkyl.

The term "aryl", alone or in combination, includes a carbocyclic aromatic system containing one, two or three rings wherein such rings may be attached together in a pendent manner or may be fused. Examples of aryl groups include phenyl, benzyl, naphthyl, and biphenyl. The "aryl" group can be optionally substituted where possible with one or more of the moieties including but not limited to alkyl, hydroxyl, halo, nitro, cyano, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that preferably does not inhibit the pharmacological activity of the compound, either unprotected, or protected as necessary, as known to those skilled in the art. In addition, adjacent groups on an "aryl" ring may combine to form a 5- to 7-membered saturated or partially unsaturated carbocyclic, aryl, heteroaryl or heterocyclic ring, which in turn may be substituted as above.

The term "halo" includes fluoro, bromo, chloro, and iodo.

The term "heterocyclic" includes nonaromatic cyclic groups that may be partially (e.g., contains at least one double bond) or fully saturated and wherein there is at least one heteroatom, such as oxygen, sulfur, nitrogen, or phosphorus in the ring. Similarly, the term heteroaryl or heteroaromatic, as used herein, refers to an aromatic that includes at least one sulfur, oxygen, nitrogen or phosphorus in the aromatic ring. Nonlimiting examples of heterocyclics and heteroaromatics include pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl wherein the heteroaryl or heterocyclic group can be optionally substituted with one or more substituent selected, for example, from the same substituents as set out above for aryl groups. Functional oxygen and nitrogen groups on the heteroaryl group can be protected as necessary or as desired. Suitable protecting groups can include but are not limited to trimethylsilyl (TMS), dimethylhexylsilyl (DMHS), t-butyldimethylsilyl (TBS or TBDMS), and t-butyldiphenylsilyl (TBDPS), trityl (Trt) or substituted trityl, alkyl groups, acyl (Ac) groups such as acetyl and propionyl, methanesulfonyl, and p-toluenelsulfonyl.

The terms "protecting group" or "protected" refers to a substituent that protects various sensitive or reactive groups present, so as to prevent said groups from interfering with a reaction. Such protection may be carried out in a well-known manner as taught by Greene, et al., *Protective Groups in Organic Synthesis*, John Wiley and Sons, Third Edition, 1999 or the like. The protecting group may be removed after the reaction in any manner known by those skilled in the art. Non-limiting examples of protecting groups suitable for use within the present invention include but are not limited to allyl, benzyl (Bn), tertiary-butyl (t-Bu), methoxymethyl (MOM), p-methoxybenzyl (PMB), trimethylsilyl (TMS), dimethylhexylsily (TDS)I, t-butyldimethylsilyl (TBS or TBDMS), and t-butyldiphenylsilyl (TBDPS), tetrahydropyranyl (THP), trityl (Trt) or substituted trityl, alkyl groups, acyl groups such as acetyl (Ac) and propionyl, methanesulfonyl (Ms), and p-toluenesulfonyl (Ts). Such protecting groups can form, for example in the instances of protecting hydroxyl groups on a molecule: ethers such as methyl ethers, substituted methyl ethers, substituted alkyl ethers, benzyl and substituted benzyl ethers, and silyl ethers; and esters such as formate esters, acetate esters, benzoate esters, silyl esters and carbonate esters, as well as sulfonates, and borates.

III. Pharmaceutical Compositions

Pharmaceutical carriers suitable for administration of the compounds provided herein include any such carriers known to those skilled in the art to be suitable for the particular mode of administration. The compounds may be formulated as the sole pharmaceutically active ingredient in the composition or may be combined with other active ingredients.

Compositions comprising the compounds disclosed herein may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration.

The compositions may conveniently be presented in unit dosage form and may be prepared by conventional pharmaceutical techniques. Such techniques include the step of bringing into association one or more compositions of the present invention and one or more pharmaceutical carriers or excipients. The term "unit dosage form", or alternatively "unit dosage levels" as used herein refers to physically discrete units suitable as unitary dosages for human subjects, each unit containing a predetermined quantity of active material calculated to produce the desired therapeutic effect in association with the required pharmaceutical diluent, carrier, or vehicle. The specifications for the novel unit dosage forms of this invention are dictated by and are directly dependent upon (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accordance with this invention are tablets, capsules, troches, powder packets, wafers, cachets, teaspoonfuls, tablespoonfuls, dropperfuls, ampules, vials, I.V. bags, segregated multiples of any of the foregoing, and other forms as described herein.

The term "unit dosage form", or alternatively "unit dosage levels" as used herein includes, for example, physically discrete units suitable as unitary dosages for human subjects, each unit containing a predetermined quantity of active material calculated to produce the desired therapeutic effect in association with the required pharmaceutical diluent, carrier, or vehicle. The specifications for the novel unit dosage forms of this invention are dictated by and are directly dependent upon (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accordance with this invention are tablets, capsules, troches, powder packets, wafers, cachets, teaspoonfuls, tablespoonfuls, dropperfuls, ampules, vials, I.V. bags, segregated multiples of any of the foregoing, and other forms as described herein.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof may be mixed with one or more suitable pharmaceutical carriers. The compounds may be derivatized as the corresponding salts, esters, enol ethers or esters, acetals, ketals, orthoesters, hemiacetals, hemiketals, acids, bases, solvates, hydrates or prodrugs prior to formulation. The concentrations of the compounds in the compositions are effective for delivery of an amount, upon administration, that treats, prevents, or ameliorates one or more of the symptoms of the target disease or disorder. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

Compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art; for example, see Remington's Pharmaceutical Sciences, Mack Publishing Company, Easton, Pa., 15th Edition, 1975.

Compositions of the present invention suitable for topical administration in the mouth include for example, lozenges, having the ingredients in a flavored basis, usually sucrose and acacia or tragacanth; pastilles, having one or more of the compositions of the present invention in an inert basis such as gelatin and glycerin, or sucrose and acacia; and mouthwashes, having one or more of the compositions of the present invention administered in a suitable liquid carrier.

The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Compositions suitable for topical administration to the skin may be presented as ointments, creams, gels, and pastes, having one or more of the compositions administered in a pharmaceutical acceptable carrier.

Compositions for rectal administration may be presented as a suppository with a suitable base comprising, for example, cocoa butter or a salicylate.

Compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), one or more of the compositions can be admixed in an aqueous or oily solution, and inhaled or sprayed into the nasal passage.

Compositions suitable for vaginal administration may be presented as pessaries, tampons, creams, gels, pastes, foams or spray formulations containing one or more of the compositions and appropriate carriers.

Compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

Compositions may be used as the active ingredient in combination with one or more pharmaceutically acceptable carrier mediums and/or excipients. As used herein, "pharmaceutically acceptable carrier" includes any and all carriers, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

Additionally, the compositions may be combined with pharmaceutically acceptable excipients, and, optionally, sustained-release matrices, such as biodegradable polymers, to form therapeutic compositions. A "pharmaceutically acceptable excipient" includes a non-toxic solid, semi-solid or liquid filler, diluent, encapsulating material or formulation auxiliary of any type.

It will be understood, however, that the total daily usage of the compositions will be decided by the attending physician within the scope of sound medical judgment. The specific therapeutically effective dose level for any particular host will depend upon a variety of factors, including for example, the disorder being treated and the severity of the disorder; activity of the specific composition employed; the specific composition employed, the age, body weight, general health, sex and diet of the patient; the time of administration; route of administration; rate of excretion of the specific compound employed; the duration of the treatment; drugs used in combination or coincidential with the specific composition employed; and like factors well known in the medical arts. For example, it is well within the skill of the art to start doses of the composition at levels lower than those required to achieve the desired therapeutic effect and to gradually increase the dosage until the desired effect is achieved.

Compositions are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium.

Preferred unit dosage formulations are those containing a daily dose or unit, daily sub-dose, or an appropriate fraction thereof, of the administered ingredient. The dosage will depend on host factors such as weight, age, surface area, metabolism, tissue distribution, absorption rate and excretion rate. Exemplary systemic dosages for all of the herein described conditions are those ranging from 0.1 mg/kg to 500 mg/kg of body weight per day as a single daily dose or divided daily doses. Typical dosages for topical application are those ranging from 0.001 to 100% by weight of the active compound.

The therapeutically effective dose level will depend on many factors as noted above. In addition, it is well within the skill of the art to start doses of the composition at relatively low levels, and increase the dosage until the desired effect is achieved.

Compositions containing a compound disclosed herein may be used with a sustained-release matrix, which can be made of materials, usually polymers, which are degradable by enzymatic or acid-based hydrolysis or by dissolution. Once inserted into the body, the matrix is acted upon by enzymes and body fluids. A sustained-release matrix for example is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to one or more compositions of the present invention, stabilizers, preservatives, excipients, and the like. Examples of lipids are the phospholipids and the phosphatidyl cholines (lecithins), both natural and synthetic. Methods to form liposomes are known in the art.

The compounds may be formulated as aerosols for application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

Any suitable dosage can be used in the treatment or prevention of membrane-associated diseases or disorders. Non-limiting examples include: dosage levels about 0.01 to 500 mg per kg patient body weight per day which can be administered in single or multiple doses in particular, the dosage level can be about 0.1 to about 250 mg/kg per day; in one embodiment it is about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions can be provided in the form of tablets containing 1.0 to 1000 milligrams of the active ingredient, and in particular can be 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds can be administered on a regimen of 1 to 4 times per day, in one embodiment they can be administered once or twice per day.

All of the compositions, methods and/or processes disclosed and claimed herein can be made and executed without undue experimentation in light of the present disclosure. While the compositions and methods of this invention have been described in terms of various embodiments, it will be apparent to those of skill in the art that variations can be applied to the compositions, methods and/or processes and in the steps or in the sequence of steps of the methods described herein without departing from the concept and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the scope and concept of the invention.

I claim:

1. A method for treating a membrane-associated disease or disorder in a mammal comprising administering an effective amount of a lantibiotic to the mammal, wherein the membrane associated disease is xerostomia, or platelet aggregation disorder.

2. The method of claim 1, wherein the lantibiotic is the compound of Formula I:

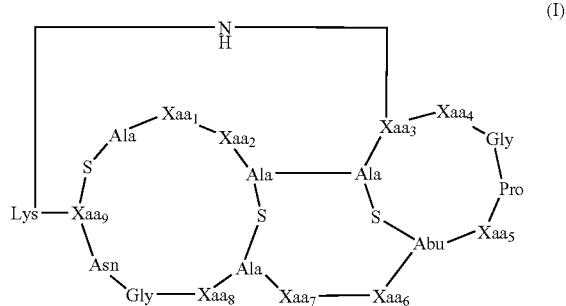

or a pharmaceutically acceptable salt thereof, wherein:

Xaa$_1$, Xaa$_2$, Xaa$_3$, Xaa$_4$, Xaa$_5$, Xaa$_6$, Xaa$_7$, Xaa$_8$, and Xaa$_9$ are independently selected from natural or synthetic amino acids.

3. The method of claim 1, wherein the lantibiotic is a Type A or Type B lantibiotic.

4. The method of claim 3, wherein the lantibiotic is a Type B lantibiotic.

5. The method of claim 4, wherein the Type B lantibiotic is duramycin.

6. The method of claim 1, wherein the lantibiotic is administered in combination or alternation with an aminoglycoside.

7. The method of claim 6, wherein the aminoglycoside is tobramycin.

8. The method of claim 1, wherein the membrane-associated disease is xerostomia.

9. The method of claim 8, wherein the xerostomia is caused by another drug or pharmaceutical agent.

10. The method of claim 9, wherein the drug or pharmaceutical agent is selected from the group consisting of anticholinergics, antispasmodics, antihypertensives, antidepressants, anticonvulsants, pain killers, anti-rejection drugs, anti-psychotics, decongestants, and antihistamines.

11. The method of claim 8, wherein the lantibiotic is administered orally.

12. The method of claim 11, wherein the lantibiotic is administered as a lozenge.

13. The method of claim 8, wherein the xerostomia is caused by an abnormal physiological state.

14. The method of claim 13, wherein the physiological state is selected from the group consisting of an infection, elevated stress, anxiety, depression, endocrine disease and autoimmune disorder.

15. The method of claim 1, wherein the membrane-associated disease is a platelet aggregating disease.

16. The method of claim 15, wherein the platelet aggregating disease is selected from the group consisting of atherosclerotic cardiovascular disease, coronary artery disease, cerebral vascular disease, kidney disease, abdominal vascular insufficiency, and peripheral vascular disease.

17. A method for treating an autoimmune disease in a mammal comprising administering an effective amount of a lantibiotic to the mammal.

18. A method for treating arthritis in a mammal comprising administering an effective amount of a lantibiotic to the mammal.

19. The method of claim 2 wherein the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, lanthionine, and α-methyllanthionine.

* * * * *